US012629181B2

(12) United States Patent
Al-Shammasi et al.

(10) Patent No.: US 12,629,181 B2
(45) Date of Patent: May 19, 2026

(54) MODULAR INTRAMEDULLARY FIXATION DEVICES

(71) Applicant: KUWAIT UNIVERSITY, Safat (KW)

(72) Inventors: Ahmed Ali Al-Shammasi, Safat (KW); Yagoub Abdulrahman Al Sayed Hashim, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 96 days.

(21) Appl. No.: 18/911,835

(22) Filed: Oct. 10, 2024

(65) Prior Publication Data

US 2025/0072942 A1      Mar. 6, 2025

Related U.S. Application Data

(63) Continuation-in-part of application No. 18/822,386, filed on Sep. 2, 2024, now abandoned, which is a continuation of application No. 17/393,645, filed on Aug. 4, 2021, now Pat. No. 12,076,062.

(51) Int. Cl.
    *A61B 17/72*           (2006.01)
(52) U.S. Cl.
    CPC ................................. *A61B 17/7283* (2013.01)
(58) Field of Classification Search
    CPC . A61B 17/7283; A61B 17/72; A61B 17/7241; A61B 17/7291
    USPC ...................................................... 606/62–68
    See application file for complete search history.

(56) References Cited

U.S. PATENT DOCUMENTS

| | | | |
|---|---|---|---|
| 5,626,580 A | | 5/1997 | Brosnahan |
| 5,879,352 A | * | 3/1999 | Filoso ................ A61B 17/7013 |
| | | | 606/62 |
| 8,216,238 B2 | | 7/2012 | Medoff |
| 9,144,506 B2 | * | 9/2015 | Phelps .................. A61F 2/4611 |
| 2008/0249628 A1 | * | 10/2008 | Altarac ................. A61F 2/4455 |
| | | | 623/17.11 |
| 2009/0228007 A1 | * | 9/2009 | Justin ................. A61B 17/7208 |
| | | | 606/62 |
| 2011/0077651 A1 | | 3/2011 | Lozier et al. |
| 2012/0065638 A1 | | 3/2012 | Moore |
| 2013/0090690 A1 | * | 4/2013 | Walsh ................ A61B 17/7023 |
| | | | 606/260 |
| 2020/0100821 A1 | | 4/2020 | Barry et al. |

* cited by examiner

FOREIGN PATENT DOCUMENTS

| | | | |
|---|---|---|---|
| FR | 2653006 A1 | 4/1991 | |
| GB | 2268068 A | 1/1994 | |

*Primary Examiner* — Eduardo C Robert
*Assistant Examiner* — Tara Rose E Carter
(74) *Attorney, Agent, or Firm* — Nath, Goldberg & Meyer; Joshua B. Goldberg

(57)           ABSTRACT

The modular intramedullary fixation device is a multi-piece bone fixation device for insertion into the medullary cavity of a bone. In one embodiment, the modular intramedullary fixation device is formed from a plurality of substantially Z-shaped modular elements, which are assembled together to a desired length and width. In additional embodiments, the modular intramedullary fixation device includes a proximal portion, a distal portion, and a connector for connecting the two portions to each other. The connector may be provided in a wide variety of configurations, including an adjustable connector for adjusting the length of the modular intramedullary fixation device. Each of the proximal and distal portions may further have an adjustable length.

2 Claims, 26 Drawing Sheets

710'

764

768

766

762

1700

1700

1700

1900

1901

1902

1903

1905

1904

1906

1907

1908

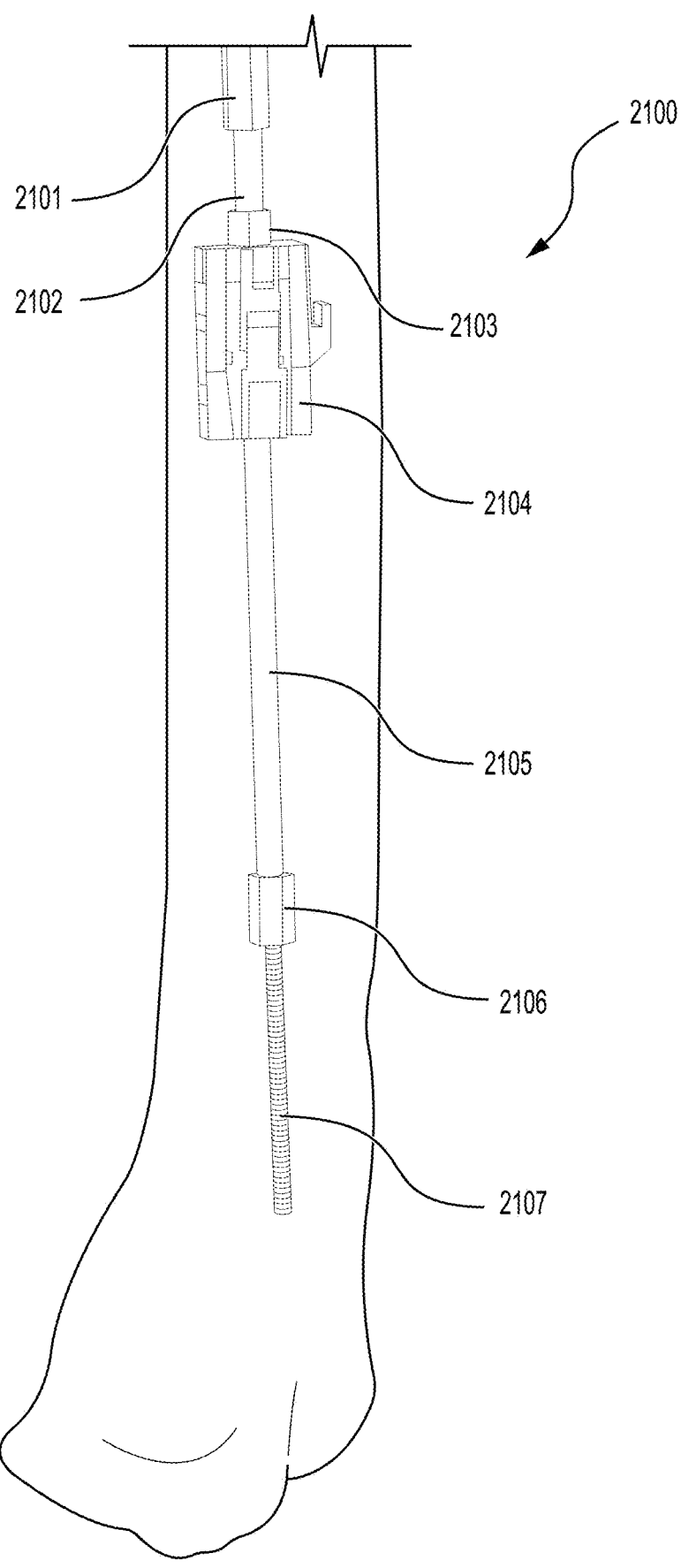
2101
2102
2103
2104
2105
2106
2107
2100
_FIG. 34_

MODULAR INTRAMEDULLARY FIXATION DEVICES

CROSS-REFERENCE TO RELATED APPLICATION

This application is a continuation-in-part of U.S. patent application Ser. No. 18/822,386, filed on Sep. 2, 2024, a continuation of U.S. patent application Ser. No. 17/393,645, filed on Aug. 4, 2021, and issued as U.S. Pat. No. 12,076,062 on Sep. 3, 2024, the entire contents of each of which are incorporated herein by reference.

BACKGROUND

1. Field

The disclosure of the present patent application relates to medical and surgical devices, and particularly to modular intramedullary fixation devices for the fixation of bones.

2. Description of the Related Art

Intramedullary fixation devices (IMFDs), such as nails and rods, are used for the fixation of various bones, and are typically used in the femur, tibia, humerus, radius and ulna. Given the wide variety of sizes and shapes of bones between different patients, great care must be taken in selecting an intramedullary device of the proper size and shape, and also in the preparation of the bone to accommodate the intramedullary device. A number of highly invasive techniques are used to treat patients by utilizing fixation devices. It would be desirable to be able to replace the conventional standards of care with a fixation device which is more adaptable for use with a variety of different patients, and which would utilize less invasive techniques. Thus, modular intramedullary fixation devices solving the aforementioned problems are desired.

SUMMARY

The modular intramedullary fixation device is a multi-piece bone fixation device adapted for insertion into the medullary cavity of a bone. In one embodiment, the modular intramedullary fixation device has a proximal section and a distal section, and is formed from a plurality of substantially Z-shaped modular elements. Each of the substantially Z-shaped modular elements has a proximal flange and a distal flange. The distal flange of each of the substantially Z-shaped modular elements is secured to the proximal flange of an adjacent one of the substantially Z-shaped modular elements. A proximal end piece is secured to the proximal flange of a proximal-most one of the substantially Z-shaped modular elements, and a distal end piece is secured to the distal flange of a distal-most one of the substantially Z-shaped modular elements.

The proximal end piece and a first portion of the substantially Z-shaped modular elements define the proximal section of the modular intramedullary fixation device, and the distal end piece and a second portion of the substantially Z-shaped modular elements define the distal section of the modular intramedullary fixation device. In order to match the dimensions of the particular bone (e.g., the ulna), a maximum width of the proximal section may be greater than a maximum width of the distal section.

Each of the proximal and distal end pieces has a passage formed therethrough for receiving a corresponding screw.

Additionally, the proximal flange of each of the substantially Z-shaped modular elements has a passage formed therethrough for receiving a corresponding screw. Similarly, the distal flange of each of the substantially Z-shaped modular elements has a passage formed therethrough for receiving a corresponding screw to secure the plurality of substantially Z-shaped modular elements, the proximal end piece and the distal end piece together.

In an alternative embodiment, the modular intramedullary fixation device is formed from a proximal portion, having opposed proximal and distal ends, and a distal portion having opposed proximal and distal ends. A distal circular flange is formed on the distal end of the proximal portion, and a proximal circular flange is formed on the proximal end of the distal portion. A circular plate, the distal circular flange and the proximal circular flange are each secured together, such that the circular plate is sandwiched there between. Each of the circular plate, the distal circular flange and the proximal circular flange has at least one passage formed therethrough for receiving at least one screw to secure the circular plate, the distal circular flange and the proximal circular flange together. In order to match the dimensions of the particular bone (e.g., the ulna), a maximum width of the proximal portion may be greater than a maximum width of the distal portion.

In another alternative embodiment, the modular intramedullary fixation device includes a proximal portion, having opposed proximal and distal ends, and a distal portion, having opposed proximal and distal ends. The proximal portion has a distal connector formed on the distal end thereof. The distal connector has an annular groove formed therein. Similarly, the distal portion has a proximal connector formed on the proximal end thereof. The proximal connector has an annular groove formed therein. A coupler is provided, having an internal proximal rib for engaging the annular groove formed in the distal connector, and an internal distal rib for engaging the annular groove formed in the proximal connector. A pair of brackets clamp the coupler, the distal connector and the proximal connector therebetween. Each of the brackets has at least one passage formed therethrough for receiving at least one screw to secure the pair of brackets together. In order to match the dimensions of the particular bone (e.g., the ulna), a maximum width of the proximal portion may be greater than a maximum width of the distal portion.

In a further alternative embodiment, the modular intramedullary fixation device includes a proximal portion, having opposed proximal and distal ends, with a distal connector formed on the distal end of the proximal portion, and a distal portion, having opposed proximal and distal ends, with a proximal connector formed on the proximal end of the distal portion. A proximal collar, having opposed proximal and distal ends, is provided for receiving the distal connector of the proximal portion. A distal annular flange is formed about the distal end of the proximal collar. Similarly, a distal collar, having opposed proximal and distal ends, is provided for receiving the proximal connector of the distal portion. A proximal annular flange is formed about the proximal end of the distal collar. The distal annular flange is secured to the proximal annular flange.

Each of the proximal and distal annular flanges may have at least one passage formed therethrough for receiving at least one screw to secure the proximal and distal annular flanges together. In order to match the dimensions of the particular bone (e.g., the ulna), a maximum width of the proximal portion may be greater than a maximum width of the distal portion.

In another alternative embodiment, the modular intramedullary fixation device includes a proximal portion, having opposed proximal and distal ends, with a distal connector formed on the distal end of the proximal portion, and a distal portion, having opposed proximal and distal ends, with a proximal connector formed on the proximal end of the distal portion. An annular collar, having opposed proximal and distal open ends, is provided such that the proximal open end receives the distal connector of the proximal portion, and the distal open end receives the proximal connector of the distal portion. The annular collar is formed from first and second semi-cylindrical portions secured to one another.

Each of the first and second semi-cylindrical portions has at least one passage formed therethrough for receiving at least one screw to secure the first and second semi-cylindrical portions together. In order to match the dimensions of the particular bone (e.g., the ulna), a maximum width of the proximal portion may be greater than a maximum width of the distal portion.

In a further alternative embodiment, the modular intramedullary fixation device includes a proximal portion having opposed proximal and distal ends and a proximal accordion linkage to adjust the length of the proximal portion. The modular intramedullary fixation device similarly includes a distal portion having opposed proximal and distal ends and a distal accordion linkage to adjust the length of the distal portion. A connector is provided for connecting the proximal end of the distal portion to the distal end of the proximal portion.

The proximal portion further includes a fixed shaft and a rotating shaft. A first end of the proximal accordion linkage is secured to the fixed shaft of the proximal portion, and a second end of the proximal accordion linkage is rotatably secured to the rotating shaft of the proximal portion. The second end of the proximal accordion linkage may include a threaded collar in threaded engagement with a threaded portion of the rotating shaft of the proximal portion. Similarly, the distal portion includes a fixed shaft and a rotating shaft. A first end of the distal accordion linkage is secured to the fixed shaft of the distal portion, and a second end of the distal accordion linkage is rotatably secured to the rotating shaft of the distal portion. The second end of the distal accordion linkage may be a threaded collar in threaded engagement with a threaded portion of the rotating shaft of the distal portion.

The connector may be adjustable to adjust the overall length of the modular intramedullary fixation device. In this embodiment, the connector includes a threaded cylinder having opposed distal and proximal ends, with the proximal end of the threaded cylinder secured to the distal end of the proximal portion, and a rotating collar having opposed open distal and proximal ends, where the rotating collar has an internal threaded surface for threadedly engaging the threaded cylinder. The open distal end of the rotating collar has a plurality of teeth formed therearound. The connector further includes a rod partially received within the rotating collar and extending through the open distal end thereof. The rod has opposed distal and proximal ends, with the distal end of the rod being secured to the proximal end of the distal portion. A gear is rotatably mounted on the rod, with the gear engaging the plurality of teeth of the rotating collar. The user may rotate the gear to drive rotation of the rotating collar which, through its threaded engagement with the threaded cylinder, moves with respect to the threaded cylinder. In this way, the user may adjust the overall length of the modular intramedullary fixation device.

Alternatively, the connector may be provided in the form of a distal connector portion secured to the proximal end of the distal portion, where the distal connector portion has a threaded engaging member, and a proximal connector portion secured to the distal end of the proximal portion, where the proximal connector portion has a threaded passage for threadedly receiving the threaded engaging member.

These and other features of the present disclosure will become readily apparent upon further review of the following specification and drawings.

BRIEF DESCRIPTION OF THE DRAWINGS

FIG. 34 is a detailed view of a modification to the first (leftmost) embodiment of the modular intramedullary fixation device of FIG. 21 shown being completed inserted within a bone fracture using a single connector from FIG. 23.

Similar reference characters denote corresponding features consistently throughout the attached drawings.

DETAILED DESCRIPTION OF THE PREFERRED EMBODIMENTS

Figure 1:
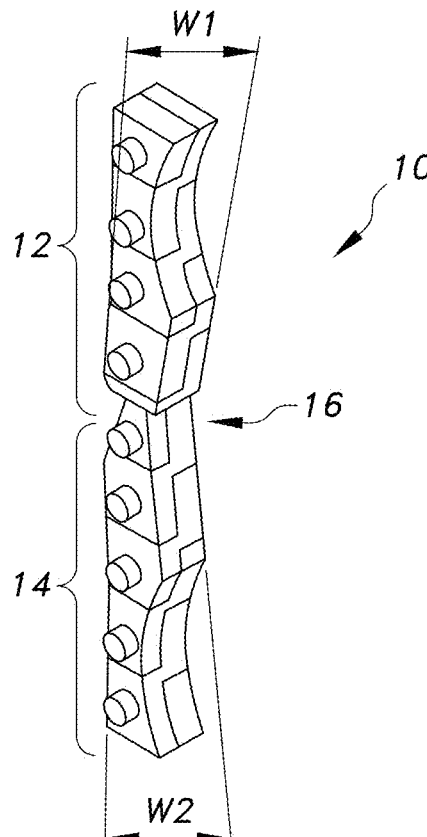
FIG. 1 is a perspective view of a modular intramedullary fixation device.
Figure 2:
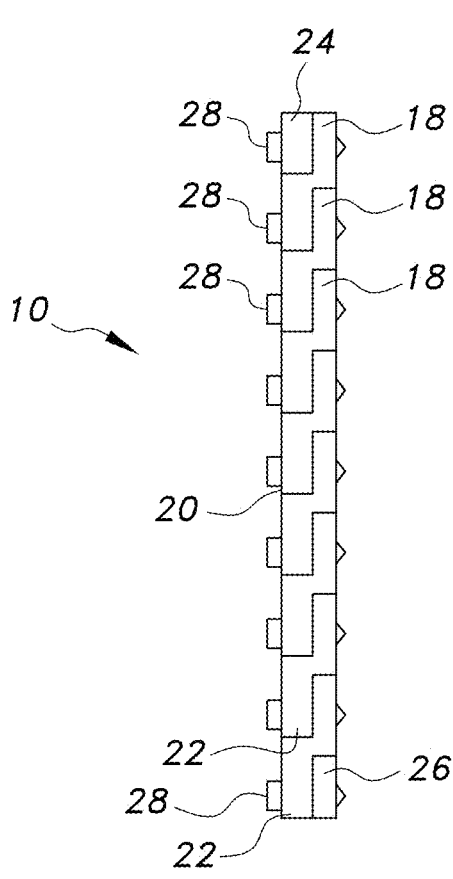
FIG. 2 is a side view of the modular intramedullary fixation device of FIG. 1.
Figure 3:
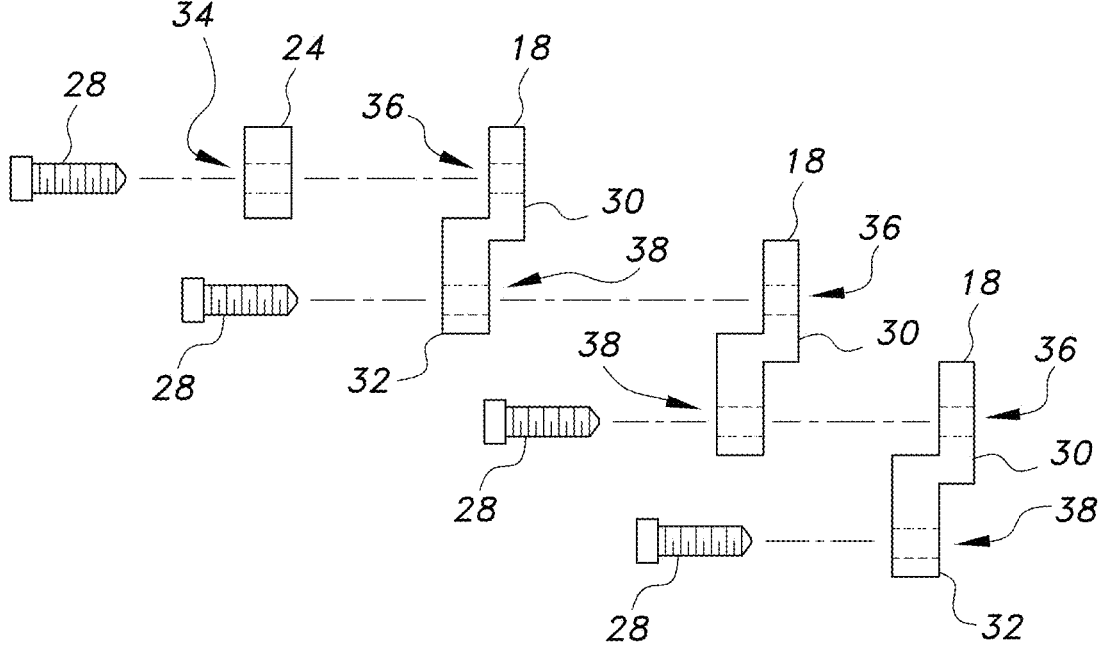
FIG. 3 is an exploded, partial side view of the modular intramedullary fixation device of FIG. 1.

The modular intramedullary fixation device 10 is adapted for insertion into the medullary cavity of a bone. In the embodiment of FIGS. 1-3, the modular intramedullary fixation device 10 has a proximal section 12 and a distal section 14, corresponding to the proximal and distal sections of the bone. The proximal section 12 is formed from a first portion of substantially Z-shaped modular elements 18, and the distal section 14 is formed from a second portion of substantially Z-shaped modular elements 22. The substantially Z-shaped modular elements 18 and 22 are substantially similar in design.

For purposes of simplification, only three of the substantially Z-shaped modular elements 18 are shown in FIG. 3. It should be understood that the method of joining the substantially Z-shaped modular elements 18, shown in FIG. 3, also applies to the substantially Z-shaped modular elements 22, and further applies to all substantially Z-shaped modular elements forming the modular intramedullary fixation device 10. It should be further understood that the number of substantially Z-shaped modular elements shown in FIGS. 1 and 2 is shown for exemplary purposes only, and that the total number of substantially Z-shaped modular elements may be varied in order to vary the length and width of the modular intramedullary fixation device 10 to match the particular bone of the particular patient.

As shown in FIG. 3, each of the substantially Z-shaped modular elements 18 has a proximal flange 30 and a distal flange 32. The distal flange 32 of each of the substantially Z-shaped modular elements 18 is secured to the proximal flange 30 of an adjacent one of the substantially Z-shaped modular elements 18. Additionally, a proximal end piece 24 is secured to the proximal flange 30 of a proximal-most one of the substantially Z-shaped modular elements 18, and a distal end piece 26 (shown in FIGS. 1 and 2) is secured to the distal flange of a distal-most one of the substantially Z-shaped modular elements 22.

The proximal end piece 24 and the first portion of the substantially Z-shaped modular elements 18 define the proximal section 12 of the modular intramedullary fixation device 10, and the distal end piece 26 and the second portion of the substantially Z-shaped modular elements 22 define the distal section 14 of the modular intramedullary fixation device 10. As shown in FIG. 1, in order to match the dimensions of the particular bone (e.g., the ulna), a maximum width W1 of the proximal section 12 may be greater than a maximum width W2 of the distal section 14.

Returning to FIG. 3, the proximal end piece 24 has a passage 34 formed therethrough for receiving a corresponding screw 28. Similarly, the distal end piece 26 also has a passage formed therethrough for receiving a corresponding one of the screws 28. Additionally, the proximal flange 30 of each of the substantially Z-shaped modular elements 18 has a passage 36 formed therethrough for receiving a corresponding one of the screws 28. Similarly, the distal flange 32 of each of the substantially Z-shaped modular elements 18 has a passage 38 formed therethrough for receiving a corresponding one of the screws 28. It should be understood that the substantially Z-shaped modular elements 22 also have similar passages for receiving corresponding ones of screws 28. Through insertion of screws 28 through aligned passages, the plurality of substantially Z-shaped modular elements 18, 22, the proximal end piece 24 and the distal end piece 26 together are secured together to form the modular intramedullary fixation device 10. It should be understood that screws 28 are shown for exemplary purposes only, and that bolts, rivets or any other suitable type of fixture may also be used to join the modular components together.

In FIGS. 1 and 2, each of the plurality of substantially Z-shaped modular elements 18, 22, a central substantially Z-shaped modular element 20 of a central section 16, the proximal end piece 24 and the distal end piece 26 are shown having an exemplary size and overall shape. It should be understood that the overall contouring and relative dimensions of each of these elements are shown for exemplary purposes only, and may be varied dependent upon the particular bone, particular procedure, particular circumstances, and particular patient.

Figure 4:
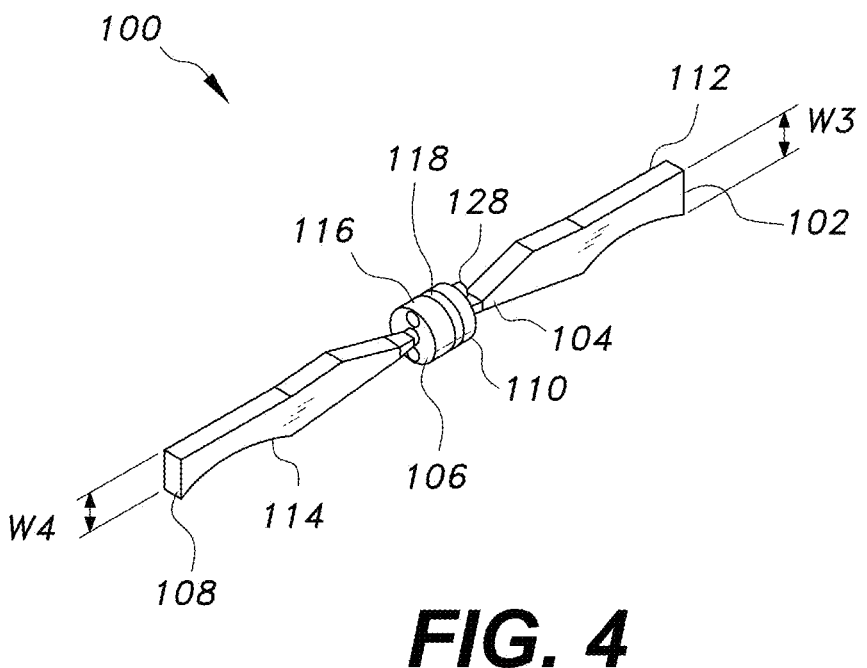
FIG. 4 is a perspective view of an alternative embodiment of the modular intramedullary fixation device.
Figure 5:
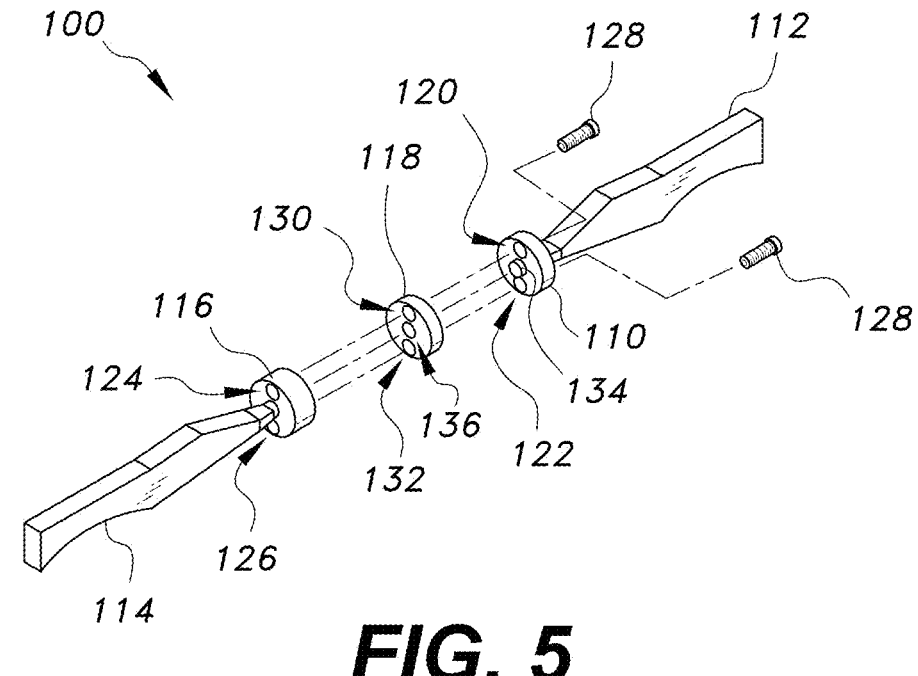
FIG. 5 is an exploded perspective view of the modular intramedullary fixation device of FIG. 4.

In the alternative embodiment of FIGS. 4 and 5, the modular intramedullary fixation device 100 is formed from a proximal portion 112, having opposed proximal and distal ends 102, 104, respectively, and a distal portion 114 having opposed proximal and distal ends 106, 108, respectively. A distal circular flange 110 is formed on the distal end 104 of the proximal portion 112, and a proximal circular flange 116 is formed on the proximal end 106 of the distal portion 114. A circular plate 118, the distal circular flange 110 and the proximal circular flange 116 are each secured together, such that the circular plate 118 is sandwiched therebetween.

In FIG. 5, circular plate 118 is shown with passages 130, 132 formed therethrough. Correspondingly, distal circular flange 110 is shown with passages 120, 122 formed therethrough, and proximal circular flange 116 is shown with passages 124, 126 formed therethrough. It should, however, be understood that these passages, for receiving corresponding screws 128, are shown for exemplary purposes only, and that any suitable number of passages may be used. Screws 128 are used to secure the circular plate 118, the distal circular flange 110 and the proximal circular flange 116 together. Additionally, as shown, circular plate 118 may have an additional central passage 134 formed therethrough for receiving an engaging rod 136, which is secured to the center of the distal circular flange 110. A similar rod may be secured to the center of the proximal circular flange 116.

In order to match the dimensions of the particular bone (e.g., the ulna), a maximum width W3 of the proximal portion 112 may be greater than a maximum width W4 of the distal portion 114. In FIGS. 4 and 5, each of the proximal portion 112, the distal portion 114, the circular plate 118, the distal circular flange 110 and the proximal circular flange 116 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 128 are shown for exemplary purposes only, and that bolts, rivets or any other suitable type of fixture may also be used to join the circular plate 118, the distal circular flange 110 and the proximal circular flange 116 together.

Figure 6:
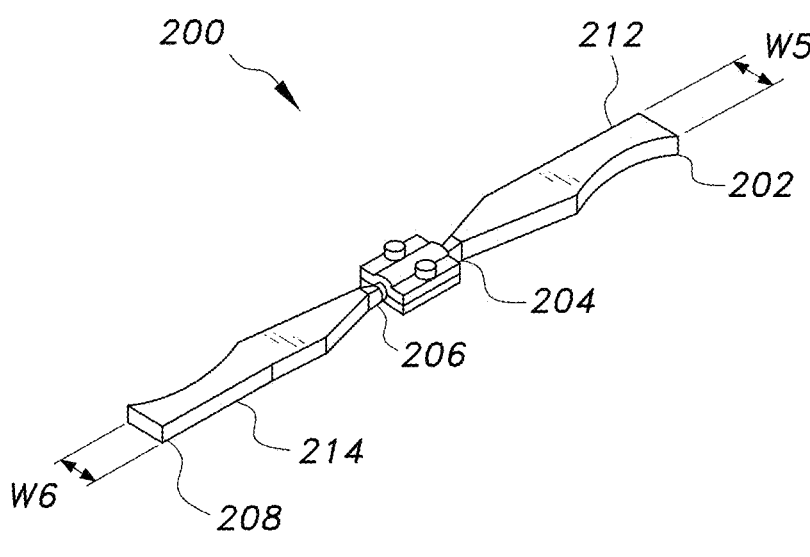
FIG. 6 is a perspective view of another alternative embodiment of the modular intramedullary fixation device.
Figure 7:
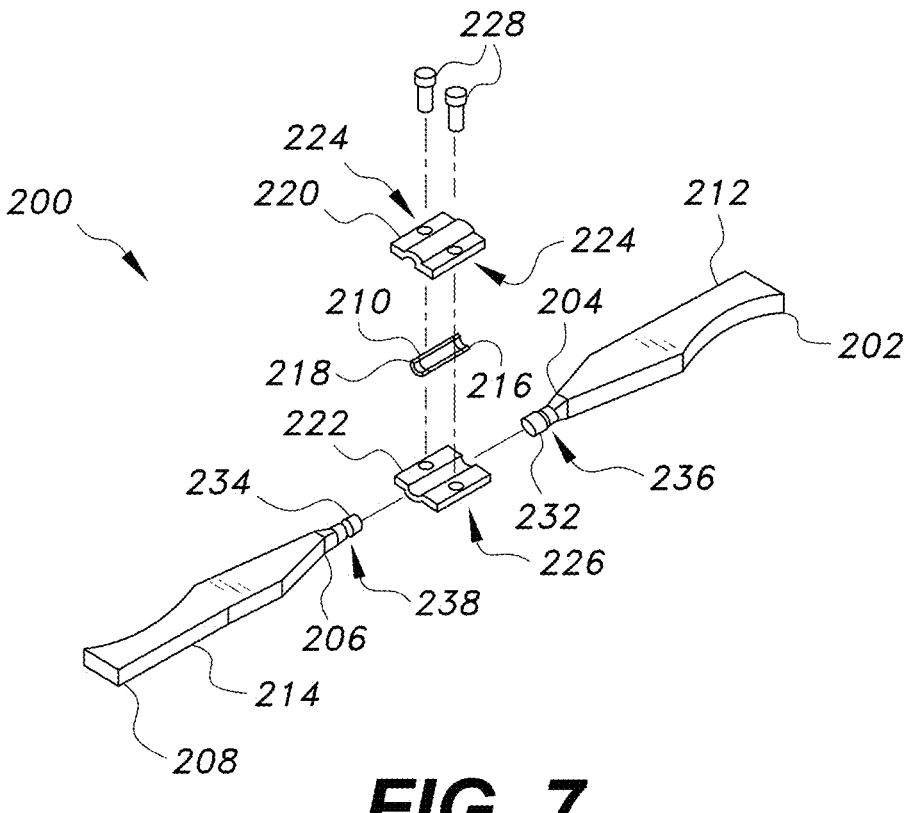
FIG. 7 is an exploded perspective view of the modular intramedullary fixation device of FIG. 6.

In the further alternative embodiment of FIGS. 6 and 7, the modular intramedullary fixation device 200 includes a proximal portion 212, having opposed proximal and distal ends 202, 204, respectively, and a distal portion 214, having opposed proximal and distal ends 206, 208, respectively. The proximal portion 212 has a distal connector 232 formed on the distal end 204. The distal connector 232 has an annular groove 236 formed therein. Similarly, the distal portion 214 has a proximal connector 234 formed on the proximal end 206. The proximal connector 234 has an annular groove 238 formed therein.

A coupler 210 is provided, having an internal proximal rib 216 for engaging the annular groove 236 formed in the distal connector 232, and an internal distal rib 218 for engaging the annular groove 238 formed in the proximal connector 234. A pair of brackets 220, 222 clamp the coupler 210, the distal connector 232 and the proximal connector 234 therebetween. Bracket 220 has at least one passage 224 formed therethrough (shown as two passages in the non-limiting example of FIGS. 6 and 7) and, similarly, bracket 222 has at least one passage 226 formed therethrough (shown as two passages in the non-limiting example of FIGS. 6 and 7). Passages 224, 226 receive corresponding screws 228 to secure the pair of brackets 220, 222 together.

In order to match the dimensions of the particular bone (e.g., the ulna), a maximum width W5 of the proximal portion 212 may be greater than a maximum width W6 of the distal portion 214. In FIGS. 6 and 7, each of the proximal portion 212, the distal portion 214, the distal connector 232, the annular groove 236, the proximal connector 234, the annular groove 238, the coupler 210 and brackets 220, 222 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 228 are shown for exemplary purposes only, and that bolts, rivets or any other suitable type of fixture may also be used to join the pair of brackets 220, 222 together.

Figures 8, 9, 10, 11:
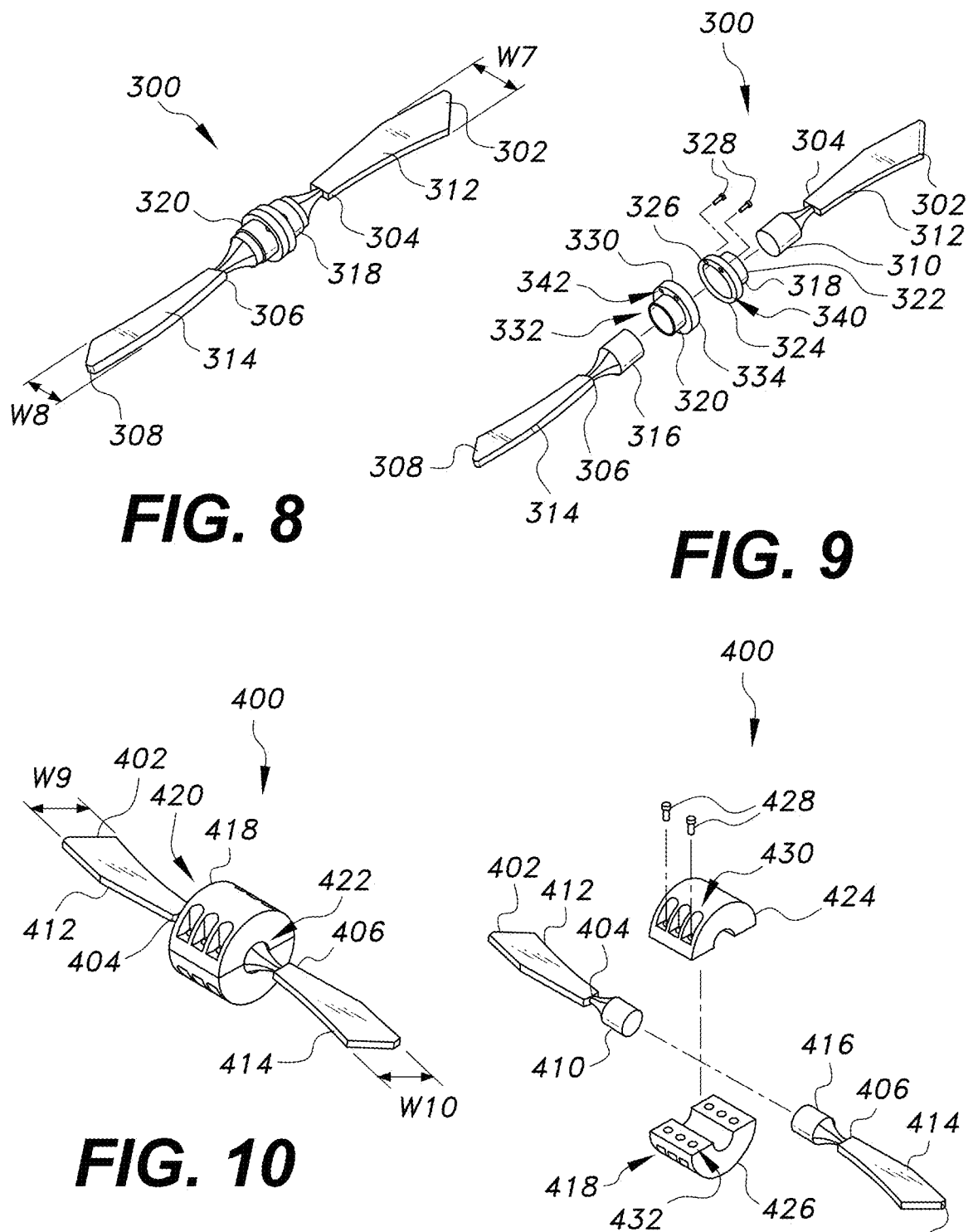
FIG. 8 is a perspective view of still another alternative embodiment of the modular intramedullary fixation device.
FIG. 9 is an exploded perspective view of the modular intramedullary fixation device of FIG. 8.
FIG. 10 is a perspective view of yet another alternative embodiment of the modular intramedullary fixation device.
FIG. 11 is an exploded perspective view of the modular intramedullary fixation device of FIG. 10.

In the further alternative embodiment of FIGS. 8 and 9, the modular intramedullary fixation device 300 includes a proximal portion 312, having opposed proximal and distal ends 302, 304, respectively, with a distal connector 310 formed on the distal end 304. The modular intramedullary fixation device 300 also includes a distal portion 314, having opposed proximal and distal ends 306, 308, respectively, with a proximal connector 316 formed on the proximal end 306. A proximal collar 318, having opposed proximal and distal ends 322, 324, respectively, is provided for receiving the distal connector 310 of the proximal portion 312. A distal annular flange 326 is formed about the distal end 324 of the proximal collar 318. Similarly, a distal collar 320, having opposed distal and proximal ends 332, 334, respectively, is provided for receiving the proximal connector 316 of the distal portion 314. A proximal annular flange 330 is formed about the proximal end 334 of the distal collar 320. The distal annular flange 326 is secured to the proximal annular flange 330.

Each of the distal and proximal annular flanges 326, 330, respectively, may have at least one passage 340, 342, respectively, formed therethrough for receiving at least one screw 328 to secure the distal and proximal annular flanges 326, 330 together. In the non-limiting example of FIGS. 8 and 9, four such passages 340 and four such passages 342 are shown, although it should be understood that any suitable number of passages (and corresponding screws 328) may be used. In order to match the dimensions of the particular bone (e.g., the ulna), a maximum width W7 of the proximal portion 312 may be greater than a maximum width W8 of the distal portion 314.

In FIGS. 8 and 9, each of the proximal portion 312, the distal portion 314, the distal connector 310, the proximal connector 316, the proximal collar 318 and the distal collar 320 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 328 are shown for exemplary purposes only, and that bolts, rivets or any other suitable type of fixture may also be used to join the distal annular flange 326 and the proximal annular flange 330 together.

In the additional alternative embodiment of FIGS. 10 and 11, the modular intramedullary fixation device 400 includes a proximal portion 412, having opposed proximal and distal ends 402, 404, respectively, with a distal connector 410 formed on the distal end 404. The modular intramedullary fixation device 400 also includes a distal portion 414, having opposed proximal and distal ends 406, 408, respectively, with a proximal connector 416 formed on the proximal end 406. An annular collar 418, having opposed proximal and distal open ends 420, 422, respectively, is provided such that the proximal open end 420 receives the distal connector 410 of the proximal portion 412, and the distal open end 422 receives the proximal connector 416 of the distal portion 414. The annular collar 418 is formed from first and second semi-cylindrical portions 424, 426, respectively, secured to one another.

Each of the first and second semi-cylindrical portions 424, 426, respectively, may have at least one passage 430, 432, respectively, formed therethrough for receiving at least one screw 428 to secure the first and second semi-cylindrical portions 424, 426 together. In the non-limiting example of FIGS. 10 and 11, three such passages 430 and three such passages 432 are shown, although it should be understood that any suitable number of passages (and corresponding screws 428) may be used. In order to match the dimensions of the particular bone (e.g., the ulna), a maximum width W9 of the proximal portion 412 may be greater than a maximum width W10 of the distal portion 414.

In FIGS. 10 and 11, each of the proximal portion 412, the distal portion 414, the distal connector 410, the proximal connector 416, and the annular collar 418 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that screws 428 are shown for exemplary purposes only, and that bolts, rivets or any other suitable type of fixture may also be used to join the first and second semi-cylindrical portions 424, 426 together.

Figure 12:
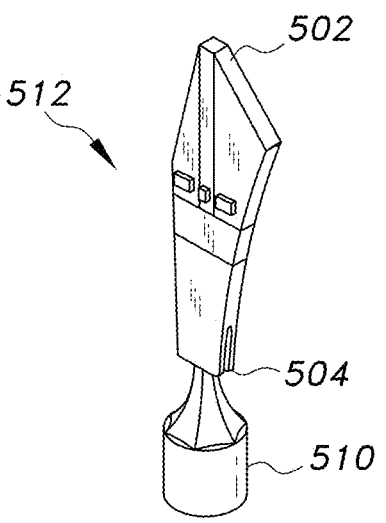
FIG. 12 is a perspective view of an alternative portion for use with the modular intramedullary fixation devices.
Figure 13:
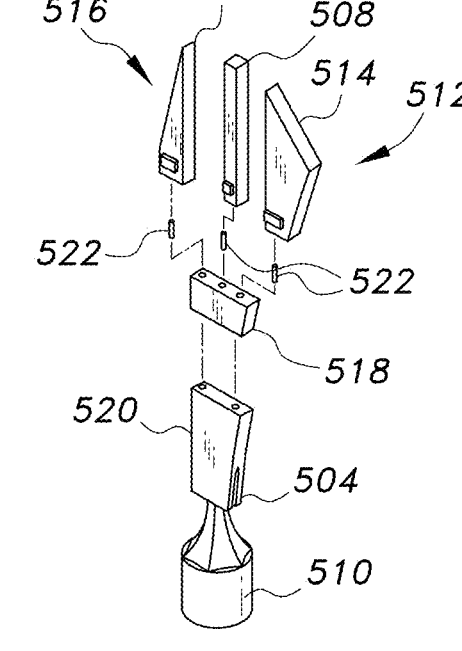
FIG. 13 is an exploded perspective view of the alternative portion of FIG. 12.

FIGS. 12 and 13 show an alternate portion 512, which has opposed proximal and distal ends 502, 504, respectively, with a distal connector 510 formed on the distal end 504. As shown in FIG. 13, a proximal region 516 of alternate portion 512 is formed from three separate panels 506, 508, 514. It should, however, be understood that proximal region 516 may be formed from any desired number of panels, and that the three panels 506, 508, 514 shown in FIG. 13 are shown for exemplary purposes only. The three panels 506, 508, 514 of proximal region 516 are secured to a central panel 518, and central panel 518 is secured to a distal panel 520. Panels 506, 508, 514, 518, 520 are all secured together by a set of internal rods 522.

In FIGS. 12 and 13, each of the panels 506, 508, 514, 518, 520, the distal connector 510, and rods 522 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that rods 522 are shown for exemplary purposes only, and that dowels, pegs or any other suitable type of fixture may also be used to join panels 506, 508, 514, 518, 520 together.

It should be further understood that alternate portion 512 may replace proximal portion 312 and/or distal portion 314 of modular intramedullary fixation device 300, or proximal portion 412 and/or distal portion 414 of modular intramedullary fixation device 400. Further, connector 510 may be modified to resemble the circular flanges of modular intramedullary fixation device 100, allowing alternate portion 512 to replace proximal portion 112 and/or distal portion 114 of modular intramedullary fixation device 100. Similarly, connector 510 may be modified to resemble the connectors of modular intramedullary fixation device 200, allowing alternate portion 512 to replace proximal portion 212 and/or distal portion 214 of modular intramedullary fixation device 200.

Figure 14:
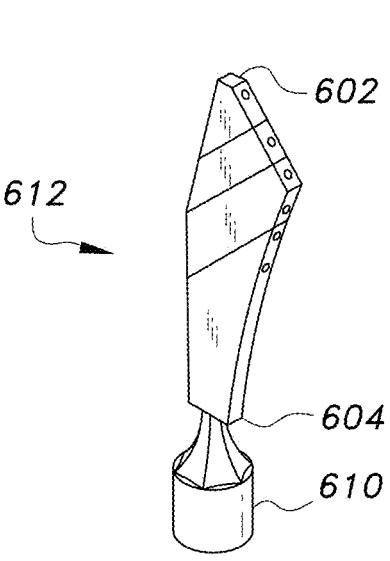
FIG. 14 is a perspective view of another alternative portion for use with the modular intramedullary fixation devices.
Figure 15:
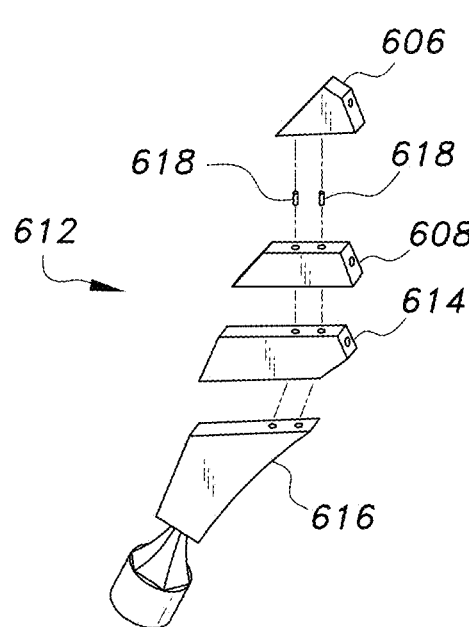
FIG. 15 is an exploded perspective view of the alternative portion of FIG. 14.

FIGS. 14 and 15 show another alternate portion 612, which has opposed proximal and distal ends 602, 604, respectively, with a distal connector 610 formed on the distal end 604. As shown in FIG. 15, a proximal panel 606 is secured to a first central panel 608, which is secured to a second central panel 614. The second central panel 614 is secured to a distal panel 616. Panels 606, 608, 614, 616 are all secured together by a set of internal rods 618.

In FIGS. 14 and 15, each of the panels 606, 608, 614, 616, the distal connector 610, and rods 618 are shown having an exemplary size and overall shape. It should be understood that the overall contouring and relative dimensions of each of these elements are shown for exemplary purposes only, and may be varied dependent upon the particular bone, particular procedure, particular circumstances and particular patient. Additionally, it should be understood that rods 618 are shown for exemplary purposes only, and that dowels, pegs or any other suitable type of fixture may also be used to join panels 606, 608, 614, 616 together.

It should be further understood that alternate portion 612 may replace proximal portion 312 and/or distal portion 314 of modular intramedullary fixation device 300, or proximal portion 412 and/or distal portion 414 of modular intramedullary fixation device 400. Further, connector 610 may be modified to resemble the circular flanges of modular intramedullary fixation device 100, allowing alternate portion 612 to replace proximal portion 112 and/or distal portion 114 of modular intramedullary fixation device 100. Similarly, connector 610 may be modified to resemble the connectors of modular intramedullary fixation device 200, allowing alternate portion 612 to replace proximal portion 212 and/or distal portion 214 of modular intramedullary fixation device 200.

Each of the previous embodiments may be implemented using a bone graft material. In the further alternative embodiment of FIG. 16, the modular intramedullary fixation device 700 may be formed from metal, such as, for example, a titanium-vanadium composite. The modular intramedullary fixation device 700 includes a proximal portion 712 having opposed proximal and distal ends 702, 704, respectively, and a proximal accordion linkage 716 to adjust the length of the proximal portion 712. The modular intramedullary fixation device 700 similarly includes a distal portion 714 having opposed proximal and distal ends 706, 708, respectively, and a distal accordion linkage 718 to adjust the length of the distal portion 714. A connector 710 is provided for connecting the proximal end 706 of the distal portion 714 to the distal end 704 of the proximal portion 712.

Figure 17A:
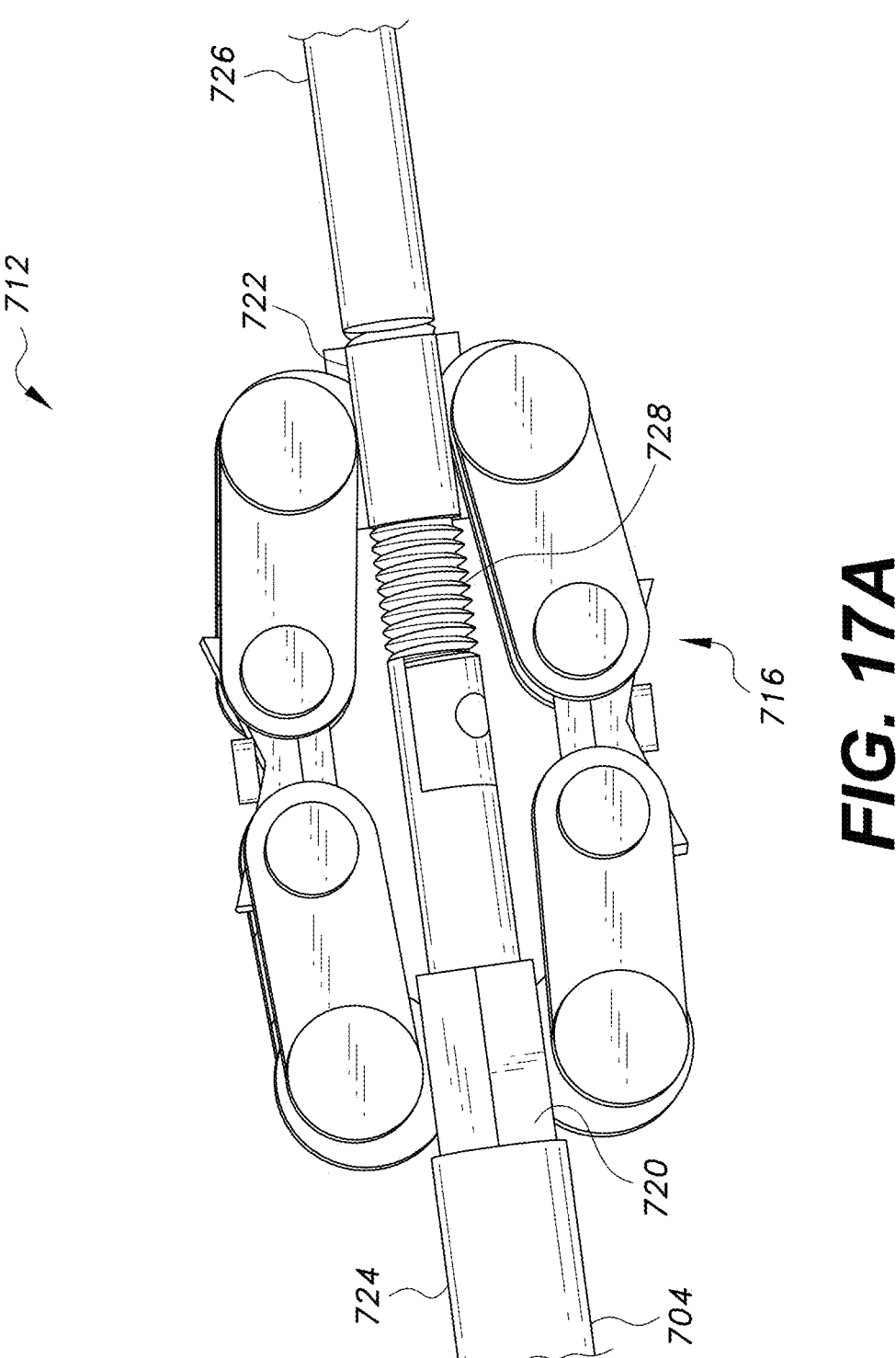
FIG. 17A is a side view of a proximal accordion linkage of the modular intramedullary fixation device of FIG. 16.

As best seen in FIG. 17A, the proximal portion 712 further includes a fixed shaft 724 and a rotating shaft 726. A first end 720 of the proximal accordion linkage 716 is secured to the fixed shaft 724 of the proximal portion 712, and a second end 722 of the proximal accordion linkage 716 is rotatably secured to the rotating shaft 726 of the proximal portion 712. The second end 722 of the proximal accordion linkage 716 may be a threaded collar in threaded engagement with a threaded portion 728 of the rotating shaft 726 of the proximal portion 712.

Figure 17B:
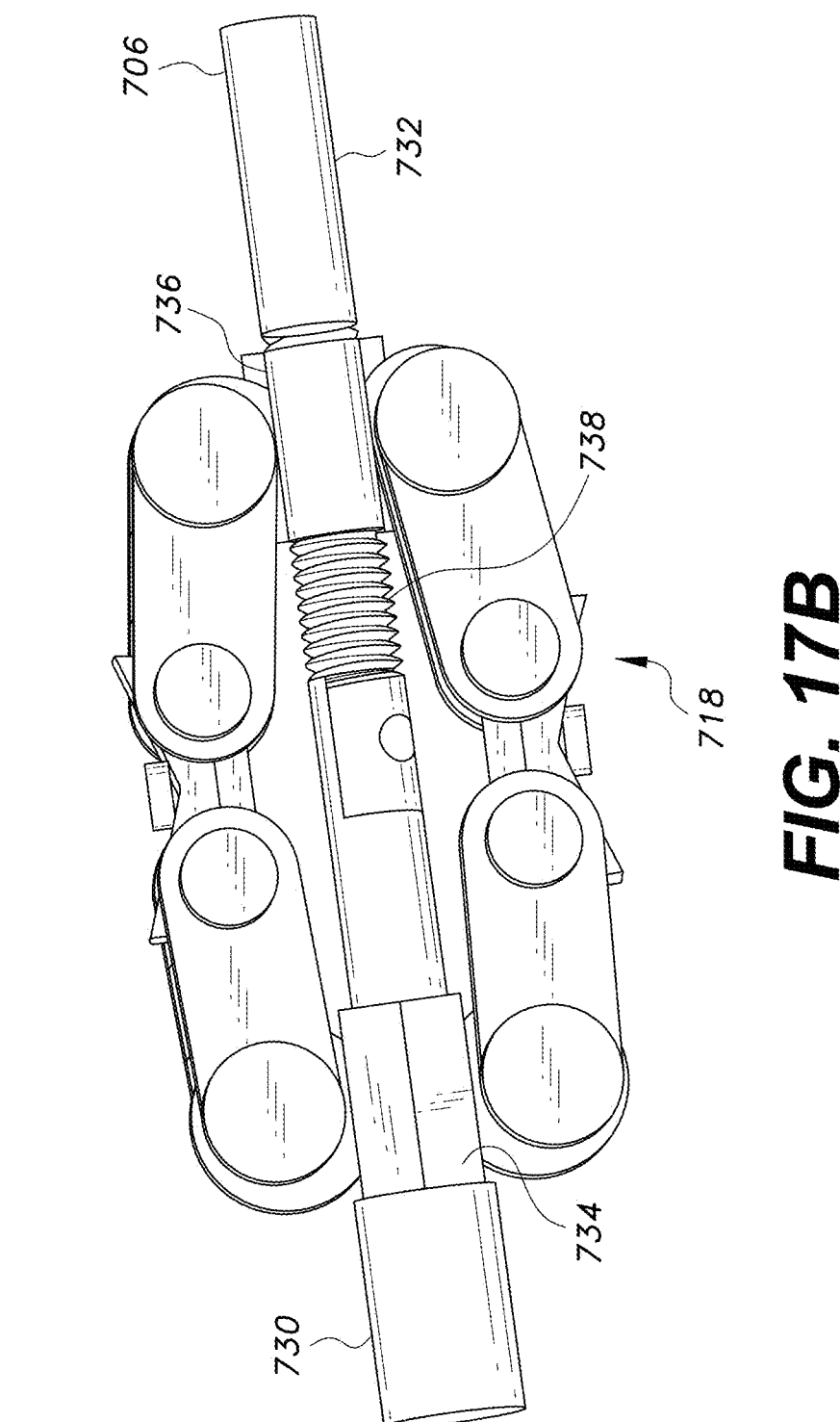
FIG. 17B is a side view of a distal accordion linkage of the modular intramedullary fixation device of FIG. 16.

Similarly, as best seen in FIG. 17B, the distal portion 714 includes a fixed shaft 730 and a rotating shaft 732. A first end 734 of the distal accordion linkage 718 is secured to the fixed shaft 730 of the distal portion 714, and a second end 736 of the distal accordion linkage 718 is rotatably secured to the rotating shaft 732 of the distal portion 714. The second end 736 of the distal accordion linkage 718 may be a threaded collar in threaded engagement with a threaded portion 738 of the rotating shaft 732 of the distal portion 714.

Figure 16:
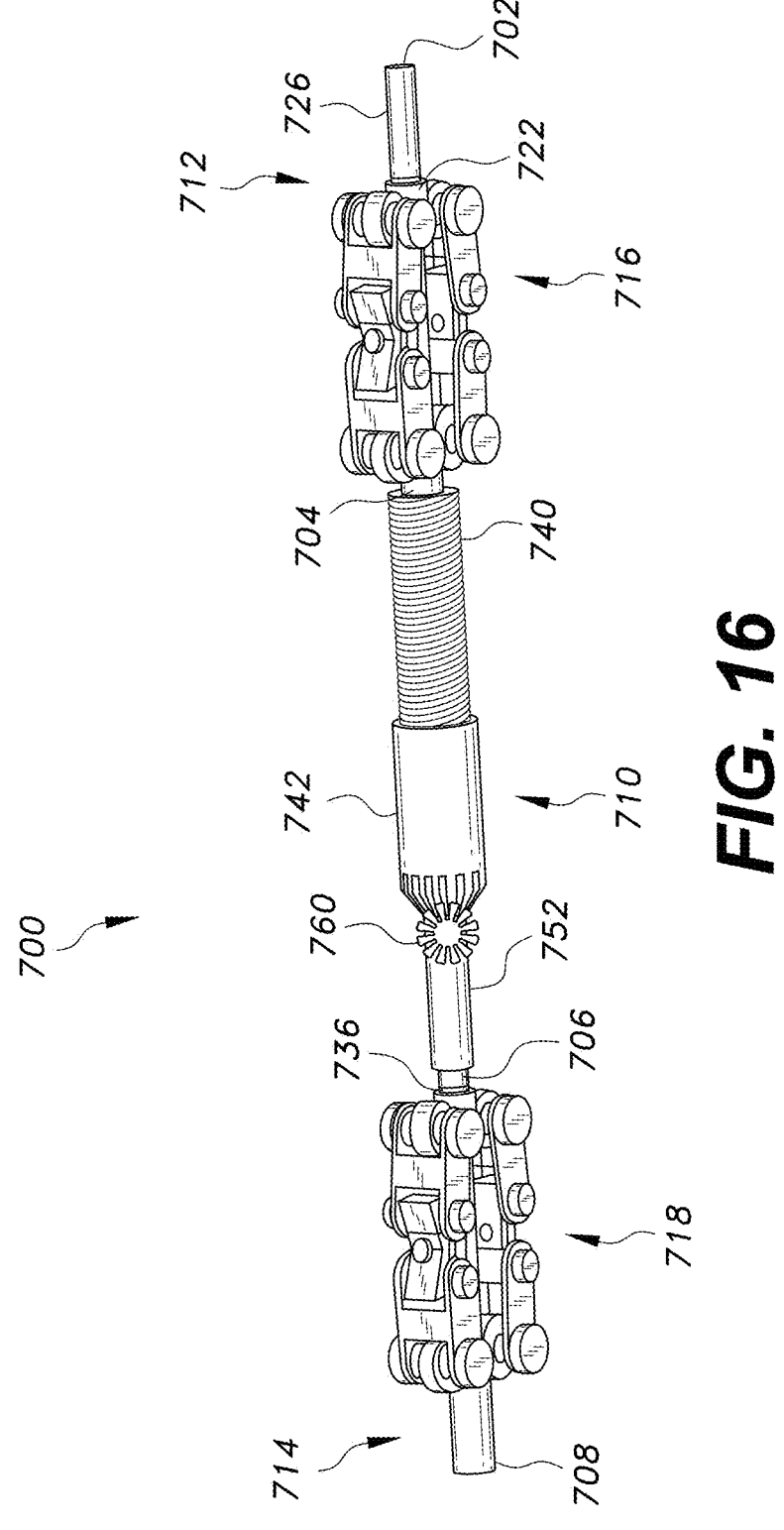
FIG. 16 is a perspective view of another alternative embodiment of the modular intramedullary fixation device.
Figure 18:
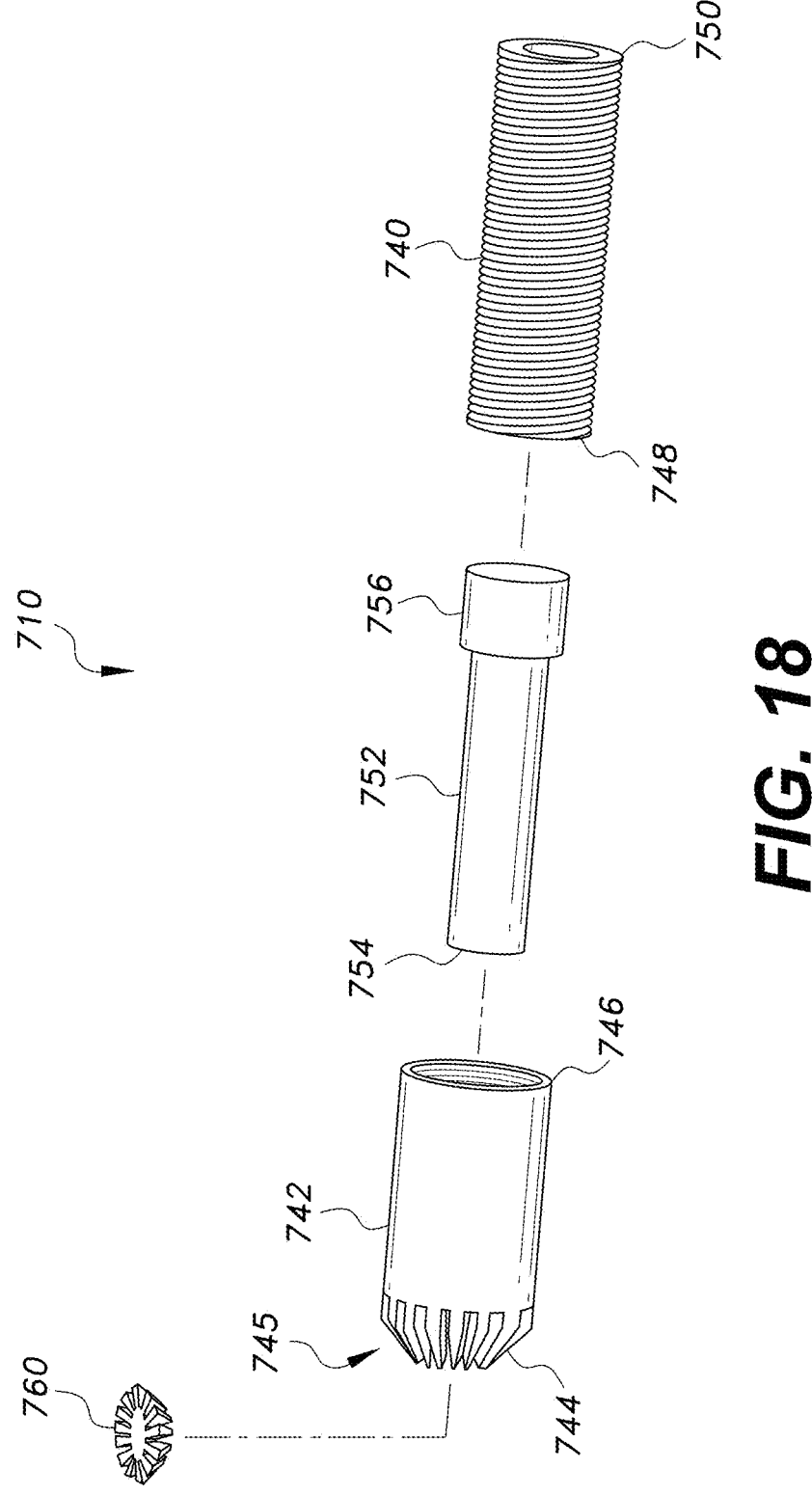
FIG. 18 is an exploded perspective view of a connector of the modular intramedullary fixation device of FIG. 16.

The connector 710 may be adjustable to adjust the overall length of the modular intramedullary fixation device 700. As shown in FIGS. 16 and 18, the connector 710 may include a threaded cylinder 740 having opposed distal and proximal ends 748, 750, respectively, with the proximal end 750 of the threaded cylinder 740 secured to the distal end 704 of the proximal portion 712. The connector 710 further includes a rotating collar 742 having opposed open distal and proximal ends 744, 746, respectively, with the rotating collar 742 having an internal threaded surface for threadedly engaging the threaded cylinder 740. The open distal end 744 of the rotating collar 742 has a plurality of teeth 745 formed therearound.

The connector 710 further includes a rod 752 partially received within the rotating collar 742 and extending through the open distal end 744. The rod 752 has opposed distal and proximal ends 754, 756, respectively, with the distal end 754 of rod 752 being secured to the proximal end 746 of the distal portion 714. A gear 760 is rotatably mounted on the rod 752, with the gear 760 engaging the plurality of teeth 745 of the rotating collar 742. The user may rotate the gear 760 to drive rotation of the rotating collar 742 which, through its threaded engagement with the threaded cylinder 740, moves with respect to the threaded cylinder 740. In this way, the user may adjust the overall length of the modular intramedullary fixation device 700.

Figure 19:
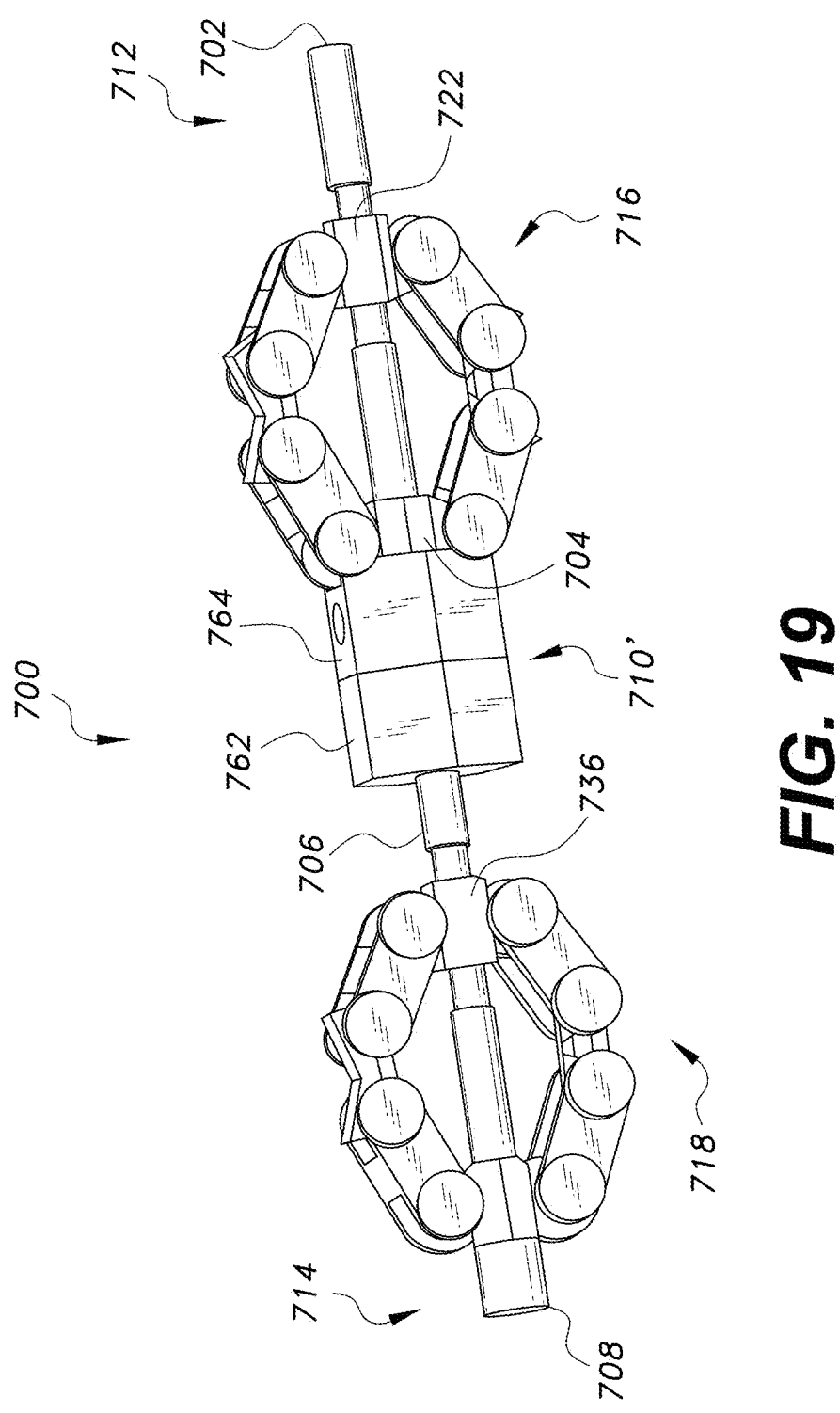
FIG. 19 is a perspective view of another alternative embodiment of the modular intramedullary fixation device.
Figure 20:
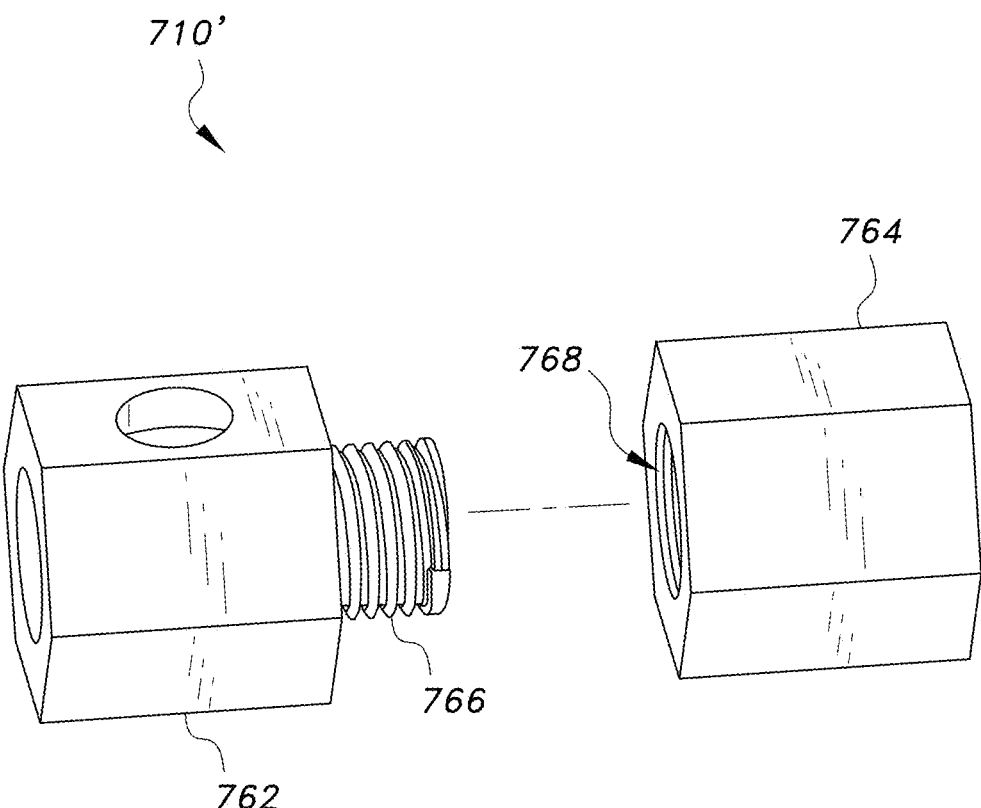
FIG. 20 is an exploded perspective view of a connector of the modular intramedullary fixation device of FIG. 19.

Alternatively, as shown in FIGS. 19 and 20, connector 710 may be replaced by alternative connector 710'. Connector 710' includes a distal connector portion 762, which is secured to the proximal end 706 of the distal portion 714, and has a threaded engaging member 766. The alternative connector 710' also includes a proximal connector portion 764, which is secured to the distal end 704 of the proximal portion 712, and has a threaded passage 768 for threadedly receiving the threaded engaging member 766.

As best seen in FIG. 17A, the proximal portion 712 further includes a fixed shaft 724 and a rotating shaft 726. A first end 720 of the proximal accordion linkage 716 is secured to the fixed shaft 724 of the proximal portion 712, and a second end 722 of the proximal accordion linkage 716 is rotatably secured to the rotating shaft 726 of the proximal portion 712. The second end 722 of the proximal accordion linkage 716 may be a threaded collar in threaded engagement with a threaded portion 728 of the rotating shaft 726 of the proximal portion 712.

Figure 21:
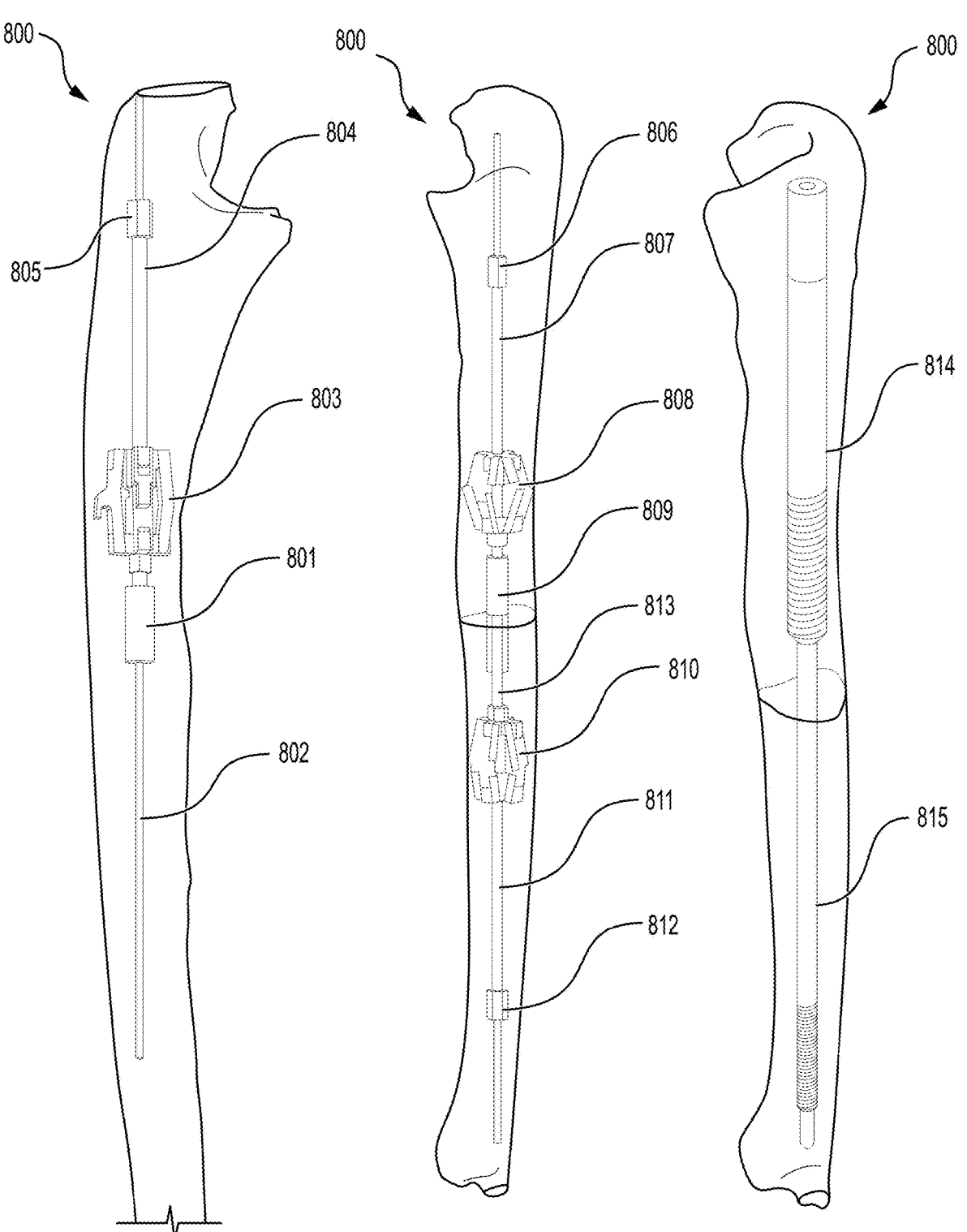
FIG. 21 is side view of three alternative embodiments of the modular intramedullary fixation device within a bone.

FIG. 21 discloses three alternative embodiments of the modular intramedullary fixation device 800 including a first embodiment (leftmost) which discloses the use of one proximal accordion linkage 803 in a collapsed configuration that is secured to a distal end of a proximal rod 804. The proximal end of the first rod 804 is connected to a second rod at a proximal hexagonal connector 805, and the distal end of first rod is connected to proximal end of a distal third rod 802 with cylindrical connector 801. Both the hexagonal connector 805 and the cylindrical connector 801 are threaded at both their respective ends to receive their respective portions of the rods as shown in FIG. 21.

The second (centermost) embodiment of the modular intramedullary fixation device 800 as shown in FIG. 21 includes the use of a proximal first accordion linkage 808 and a distal second accordion linkage 810 where accordion linkage 808 is positioned proximally above the bone fracture site (dark line in the middle portion of the bone) while accordion linkage 810 is positioned distally below the bone fracture site (dark line in the middle portion of the bone). This rod and linkage configuration further includes a proximal end of a first rod 807 that is connected to a distal end of a second rod at a proximal hexagonal connector 806, and the distal end of first rod 807 is connected to proximal end of a distal third rod 813 with cylindrical connector 809. The distal second accordion linkage 810 is secured to this third rod 813 via a positioning hexagonal nut located just above the proximal end of the distal second accordion linkage 810. The proximal first accordion linkage 808 is secured to the first rod 807 by a circular collar located at the distal end of the proximal first accordion linkage 808. Both the proximal first accordion linkage 808 and the distal second accordion linkage 810 are shown expanded as they are secured in place within structure of the bone. The proximal end of the distal second accordion linkage 810 is connected to a distal end of a hexagonal nut. The distal end of the third rod 811 is connected to a fourth distal rod using a hexagonal connector 812. Both hexagonal connectors 806, 812 and cylindrical connector 809 are threaded at both their respective ends to receive their respective portions of the rods as shown in FIG. 21.

The third (rightmost) embodiment of the modular intramedullary fixation device 800 as shown in FIG. 21 includes the use of a simple configuration of threaded rods for stabilization. A first rod 814 extends from a proximal end to a distal end where the distal end of the first rod 814 is on the proximal side of the bone fracture site (dark line in the middle portion of the bone). The distal end of the first rod is threaded on its outer surface and also threaded on its inner surface such that it can receive a proximal end of a second rod 815. Here the connection point of the first and second rods, 814 and 815 is above the bone fracture site (dark line in the middle portion of the bone). The distal end of the second rod 815 is also threaded on its exterior and threaded on an interior surface so that it can receive rods of two different sizes.

Figure 22:
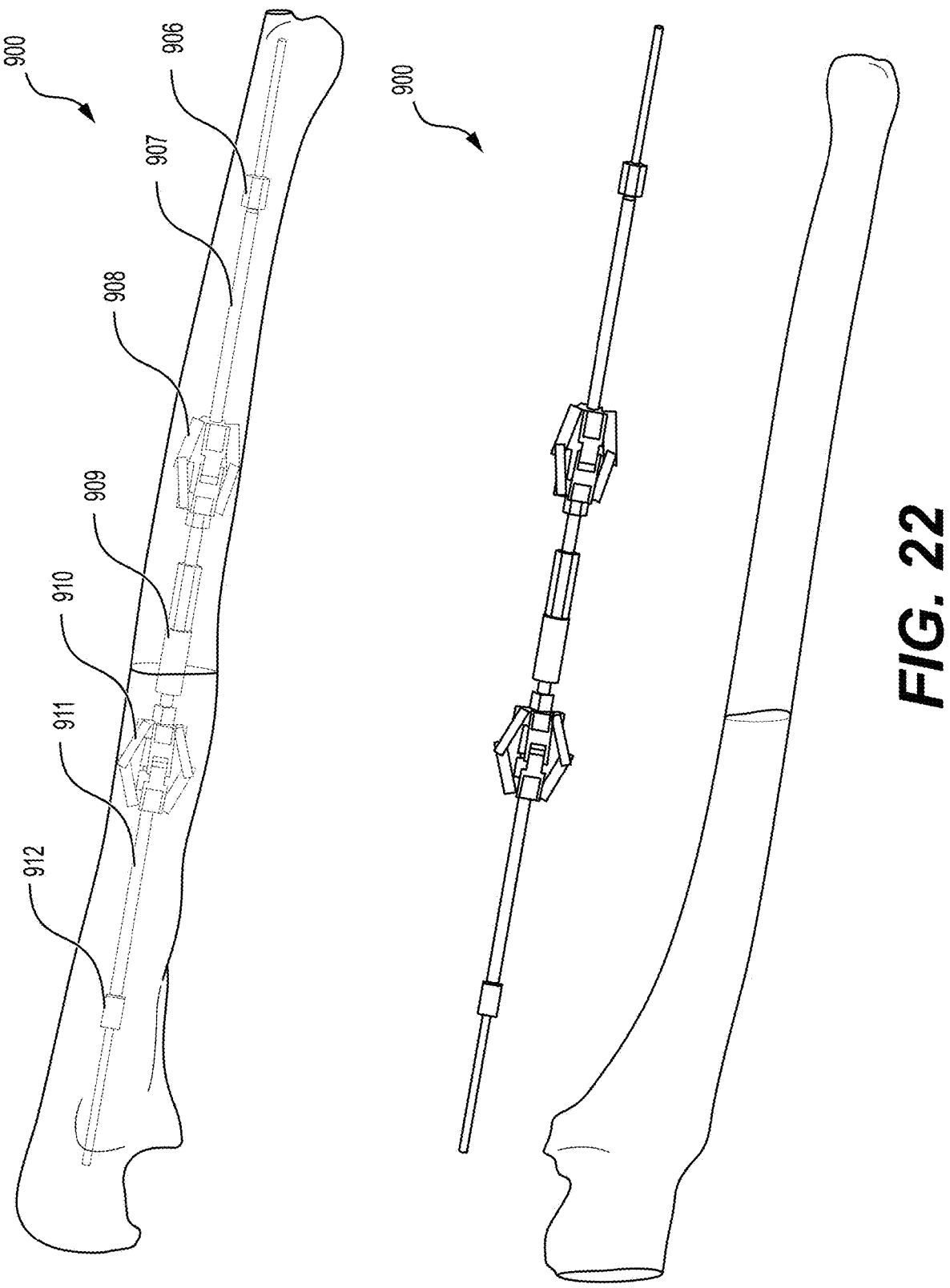
FIG. 22 is a detailed view of an alternative configuration of the second (centermost) embodiment of the modular intramedullary fixation device of FIG. 21 as inserted within the bone and as shown side by side with the fractured bone.

FIG. 22 is an alternative configuration of the second (centermost) embodiment of the modular intramedullary fixation device 800 as shown in FIG. 21. Next to the figure of the modular intramedullary fixation device 900 as inserted in the bone is a depiction of the modular intramedullary fixation device side by side with a profile of bone. This modular intramedullary fixation device 900 and also includes the use of a proximal first accordion linkage 908 and a distal second accordion linkage 910 where accordion linkage 908 is positioned proximally above the bone fracture site (dark line in the middle portion of the bone) while accordion linkage 910 is positioned distally below the bone fracture site (dark line in the middle portion of the bone). This rod and linkage configuration further includes a proximal end of a first rod 907 that is connected to a distal end of a second rod at a proximal hexagonal connector 906, and the distal end of first rod 807 is connected to proximal end of a distal third rod 911 with cylindrical connector 909. Here a hexagonal connector abuts the cylindrical connector 909 providing the modular intramedullary fixation device 900 more stability at the fracture site of the bone (dark line in the middle portion of the bone). The distal second accordion linkage 910 is secured to this third rod 911 via a positioning hexagonal nut located just above the proximal end of the distal second accordion linkage 910. The proximal first accordion linkage 908 is secured to the first rod 907 by a hexagonal nut located at its distal end. Both the proximal first accordion linkage 908 and the distal second accordion linkage 910 are shown expanded such they are secured in place within structure of the bone. The distal end of the distal second accordion linkage 910 is connected to a proximal end of a hexagonal nut 812. The distal end of the third rod 911 is connected to a fourth distal rod using a cylindrical connector 912. Hexagonal connector 806 and both cylindrical connectors 909 and 912 are threaded at both their respective ends to receive their respective portions of the rods as shown in FIG. 22.

Figure 23:
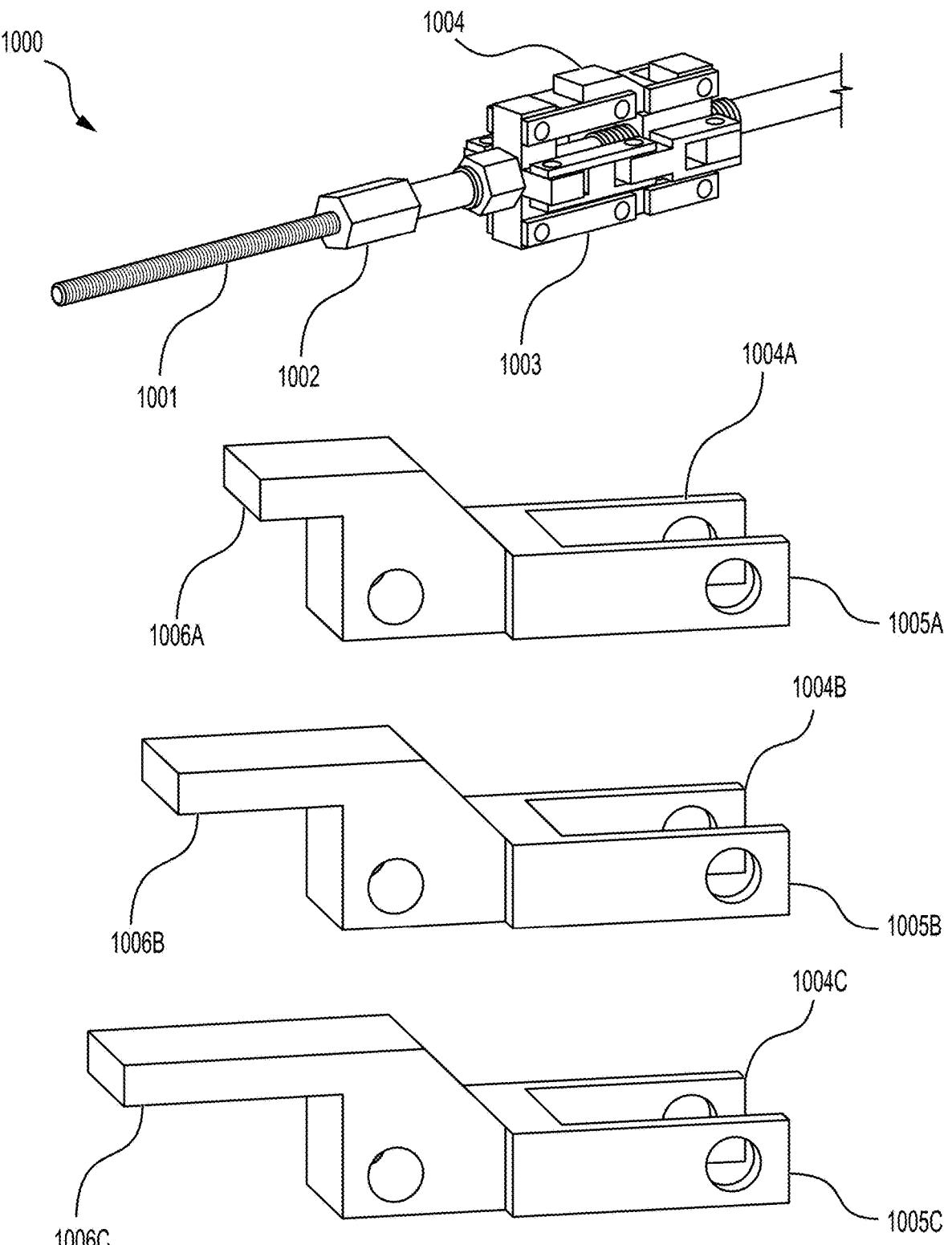
FIG. 23 is an exploded view of the connector of the first (leftmost) alternative embodiment of modular intramedullary fixation device of FIG. 21.

FIG. 23 is an alternative configuration of the first (leftmost) embodiment of the modular intramedullary fixation device 800 as shown in FIG. 21. This modular intramedullary fixation device 1000 and also includes the use of one proximal accordion linkage 1003 in a collapsed configuration that is secured to a proximal end of a first rod. The distal end of the first rod is connected to a second rod 1001 at a hexagonal connector 1002. The one proximal accordion linkage 1003 is shown a dorsal tab 1004 which can be extended to (along with the corresponding the links on the underside) into an expanded configuration as in FIGS. 21 and 22. Also, note that the specific design of the dorsal tab is customizable as shown in the three models of dorsal tabs, 1004$_A$, 1004$_B$, and 1004$_C$. Each dorsal tab from the three models has the same sized U shaped bracket 1005. Where each U shaped bracket 1005$_A$, 1005$_B$, and 1005$_C$ has a screw hole or bolt hole at the top end of each arm of the U-shaped bracket 1005$_A$, 1005$_B$, and 1005$_C$. Abutting the bottom of each U-shaped bracket 1005$_A$, 1005$_B$, and 1005$_C$ is a horizontally protruding tab with a mount base 1006$_A$, 1006$_B$, and 1006$_C$. The protruding tab with a mount base as shown in 1006$_A$, 1006$_B$, and 1006$_C$ have different sizes. The horizontally protruding tab portions have different horizontal lengths where the horizontal length of the protruding tab of 1006$_C$ is greater than the horizontal length of the protruding tab 1006$_B$, and where the horizontal length of the protruding tab of 1006$_B$ is greater than the horizontal length of the protruding tab 1006$_A$. The mount base portions of the protruding tab with a mount base are equivalent in size in all three models. Accordingly, depending upon the particular selection made by the surgeon, a careful selection of one of the dorsal tabs of 1004$_A$, 1004$_B$, and 1004$_C$ when installed for dorsal tab 1004 in the modular intramedullary fixation device 1000 can provide a range of expanded configurations of the proximal accordion linkage of FIG. 23.

Figure 24:
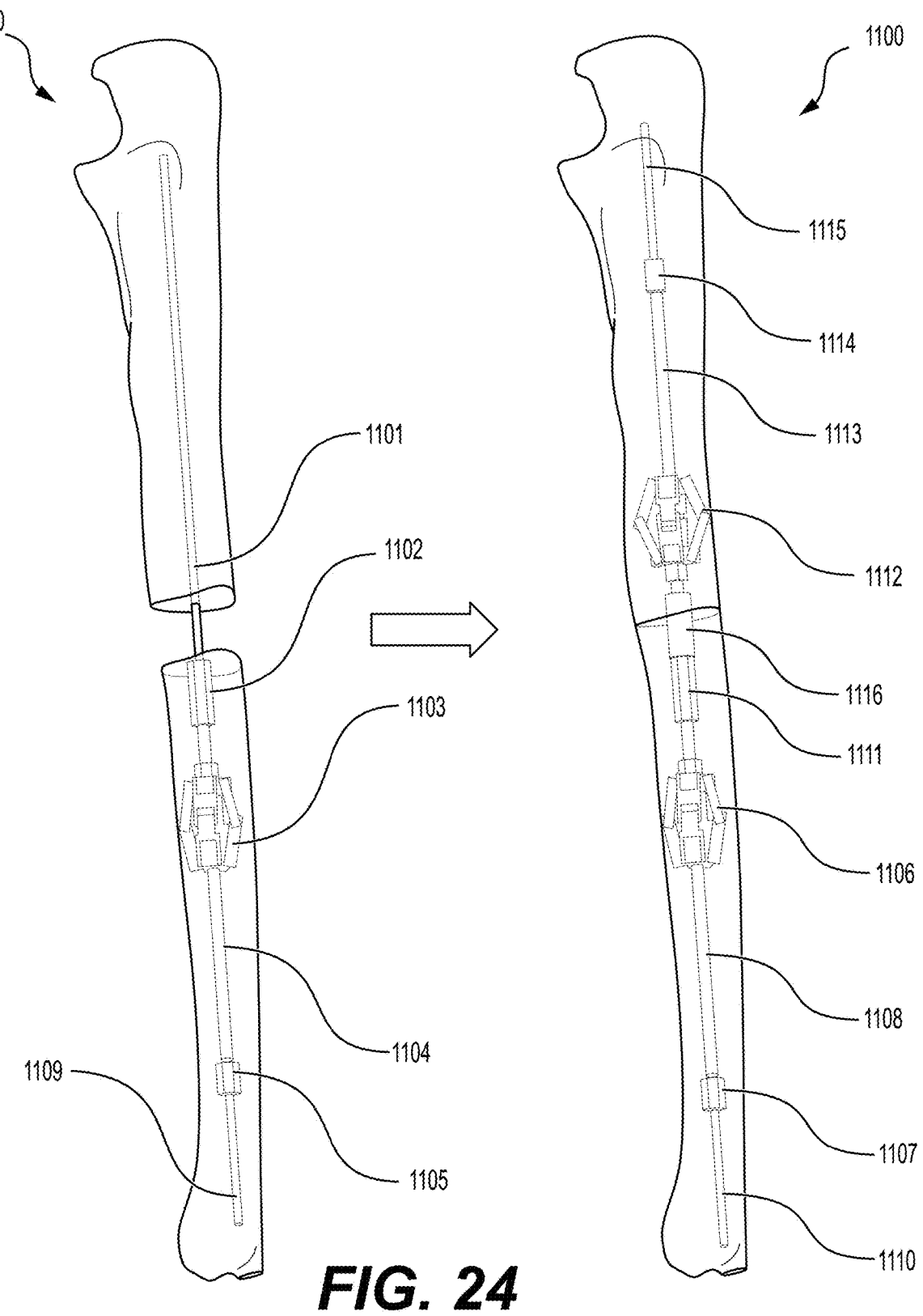
FIG. 24 is a detailed view of two alternative configurations of the second (centermost) embodiment of the modular intramedullary fixation device of FIG. 21 as inserted within the bone and as shown completely healing the break within the bone.

FIG. 24 discloses a process of modifying a first embodiment (leftmost) of FIG. 21 with the addition of parts such that it can be easily configured to be implemented as a second embodiment of FIG. 21. In FIG. 24, the modular intramedullary fixation device 1100 discloses the use of one distal accordion linkage 1103 in a collapsed configuration that is secured near a proximal end of an intermediary rod 1104. The proximal end of the intermediary rod 1104 is connected to distal end of a proximal rod 1101 at a proximal hexagonal connector 1102, and the distal end of intermediary rod 1104 is connected to proximal end of a distal third rod 1109 with hexagonal connector 1105. Both the hexagonal connectors 1102 and 1105 are threaded at both their respective ends to receive their respective portions of the rods as shown in FIG. 24. With addition of additional elements the first (leftmost) embodiment of FIG. 24 can be easily modified to the second (centermost) embodiment of the modular intramedullary fixation device 800 as shown in FIG. 21. In FIG. 24, the second (rightmost) embodiment includes a modular intramedullary fixation device 1100 which has additional elements mounted in place of the proximal rod 1101 of the first (leftmost) embodiment of the modular intramedullary fixation device 1100. The additional elements include a proximal first accordion linkage 1112 in addition to the distal second accordion linkage 1106 where accordion linkage 1112 is positioned proximally above the bone fracture site (dark line in the middle portion of the bone) while accordion linkage 1106 is positioned distally below the bone fracture site (dark line in the middle portion of the bone). This additional rod and linkage configuration further includes a proximal end of a first rod 1113 that is connected to a distal end of a second rod 1115 at a proximal cylindrical connector 1114, and the distal end of first rod 1113 is connected to proximal end of a third rod 1108 with cylindrical connector 1116 and hexagonal connector 1111. The distal second accordion linkage 1106 is secured to this third rod 1108 via a positioning hexagonal nut located just above the proximal end of the distal second accordion linkage 1106. The proximal first accordion linkage 1112 is secured to the first rod 1113 by a hexagonal nut located at the distal end of the proximal first accordion linkage 1112. Both the proximal first accordion linkage 1112 and the distal second accordion linkage 1106 are shown expanded as they are secured in place within structure of the bone. The proximal end of the distal second accordion linkage 1106 is connected to a distal end of a hexagonal nut. The distal end of the third rod 1108 is connected to a fourth distal rod 1110 using a hexagonal connector 1107. Both hexagonal connectors 1107, 1111, and cylindrical connectors 1114, 1116 are threaded at both their respective ends to receive their respective portions of the rods as shown in FIG. 21.

Figure 25:
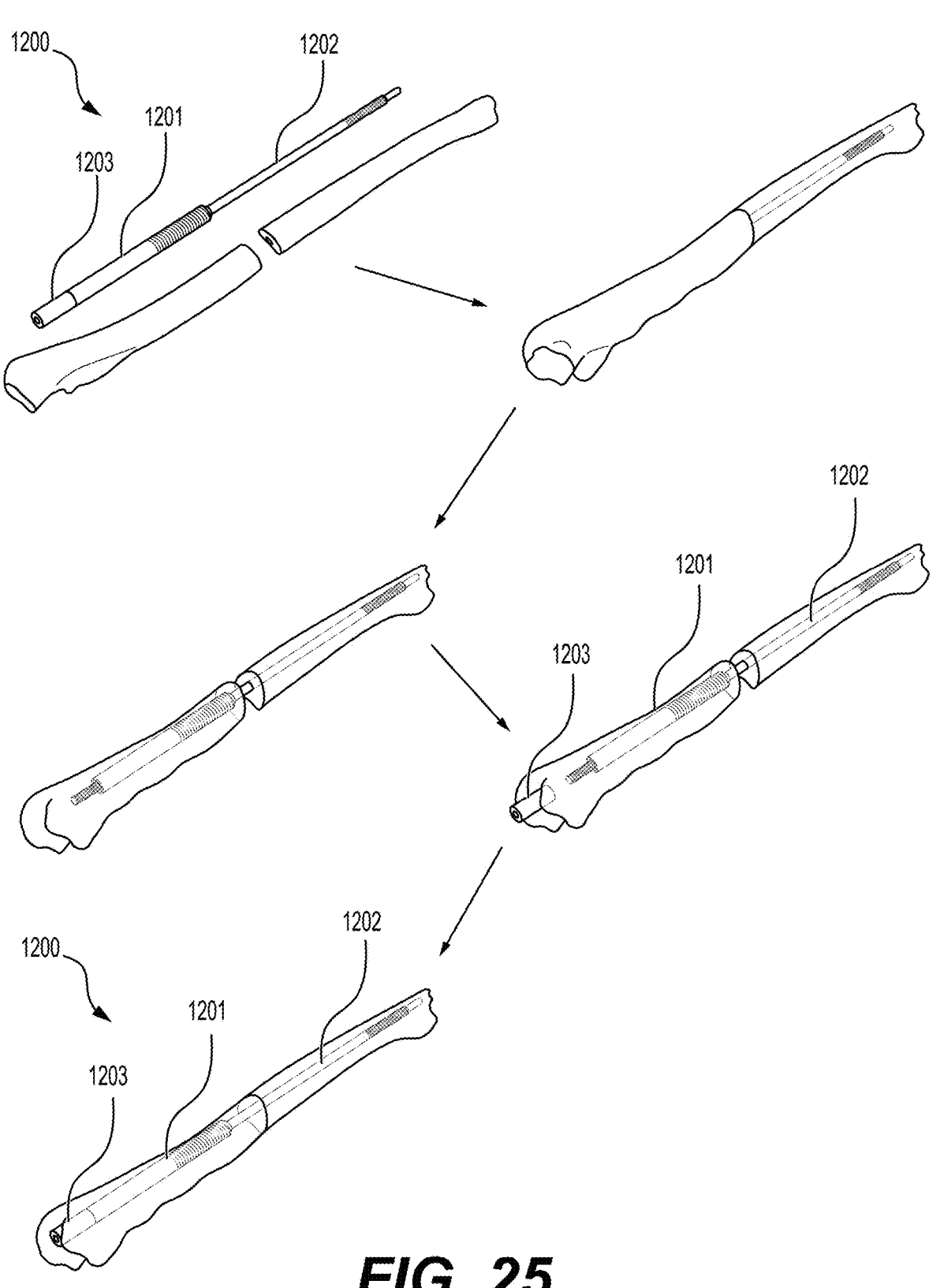
FIG. 25 is a detailed view of the third (rightmost) embodiment of the modular intramedullary fixation device of FIG. 21 shown in a progression of being side by side with the fractured bone to being inserted within the bone and completely healing the break within the bone.

FIG. 25 shows a progression in the use of the third (rightmost) embodiment of the modular intramedullary fixation device 800 as shown in FIG. 21 which relies upon the use of a simple configuration of threaded rods for stabilization. In FIG. 25, the modular intramedullary fixation device 1200 is made up for three constituent elements, a cylinder cap 1203, a first rod 1201, and a second rod 1202. The first rod 1201 extends from a proximal end to a distal end where the distal end of the first rod 1201 is on the proximal side of the bone fracture site (dark line in the middle portion of the bone). The distal end of the first rod 1201 is threaded on its outer surface and also threaded on its inner surface such that it can receive a proximal end of the second rod 1202. The proximal end of the first rod 1201 is also threaded to receive cylinder cap 1203. Here the connection point of the first and second rods, 1201 and 1202, respectively is above the bone fracture site (dark line in the middle portion of the bone). The distal end of the second rod 1202 is also threaded on its exterior and threaded on an interior surface so that it can receive rods of two different sizes. FIG. 25 shows a series of images showing the progression of the treating of a bone fracture using the modular intramedullary fixation device 1200. In FIG. 25 proceeding from top to bottom in a zig-zag fashion is the depiction of the various stages of bone fracture healing. The first stage is ensuring that prior to insertion, the combined length of the first rod 1201 and second rod 1202 can be accommodated by the lengths of the fractured bone segments. The second stage shows the insertion of the second rod 1202 into the bone fragment below the break (dark line in the middle portion of the bone. The third stage shows the insertion of the first rod 1201 into the bone fragment above the break and further depicts the connection of the first rod 1201 in the bone fragment above the break with the second rod 1202 in the bone fragment below the break such that the bone fragments are brought into proper alignment for healing. The fourth stage shows the insertion of the cylinder cap 1203 into the bone fragment above the break while also showing the connection between the first rod 1201 and the second rod 1202 is maintained. The fifth stage the attachment to the cylinder cap 1203 to the threaded distal end of the first rod 1201 and also shows the completion of the healing process where the first bone fragment and the second bone fragment have joined together and healed the break.

Figure 26:
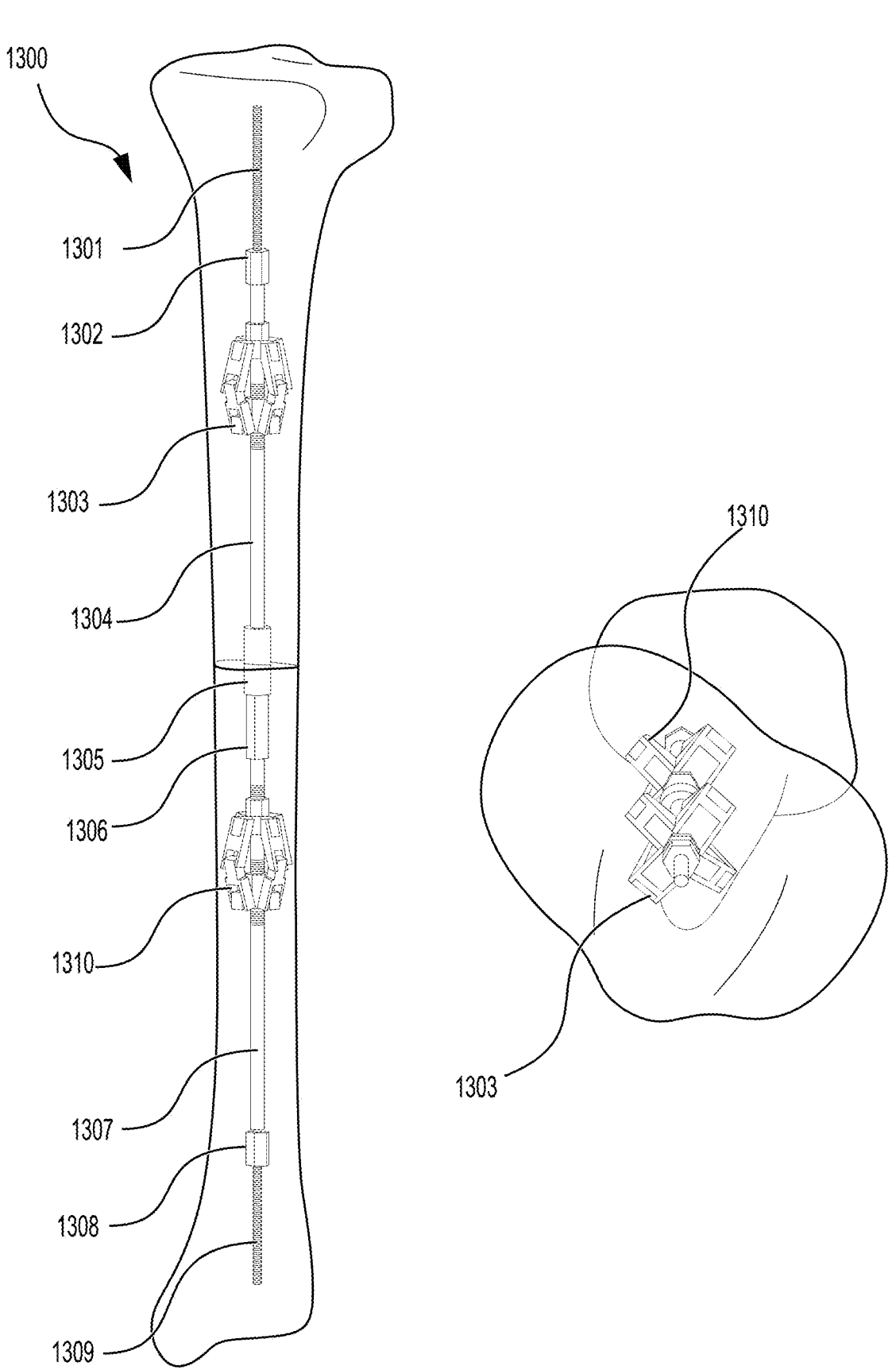
FIG. 26 is a detailed view of an alternative configuration of the second (centermost) embodiment of the modular intramedullary fixation device of FIG. 21 as inserted within the bone and as shown completely healing the break within the bone along with a top down view of the two connectors within the bone.

FIG. 26 is an alternative configuration of the second (centermost) embodiment of the modular intramedullary fixation device 800 as shown in FIG. 21. Next to the figure of the modular intramedullary fixation device 1300 as inserted in the bone is a top down view of the modular intramedullary fixation device 1300 as inserted within the bone with a specific depiction of a first proximal accordion linkage 1303 and a second distal accordion linkage 1310. The leftmost diagram shows the modular intramedullary fixation device 1300 and also includes the use of a proximal first accordion linkage 1303 and a distal second accordion linkage 1310 where the proximal first accordion linkage 1303 is positioned above the bone fracture site (dark line in the middle portion of the bone) while distal second accordion linkage 1301 is positioned below the bone fracture site (dark line in the middle portion of the bone). This rod and linkage configuration further includes a proximal end of a first rod 1304 that is connected to a distal end of a second rod 1301 at a proximal hexagonal connector 1302, and the distal end of first rod 1304 is connected to proximal end of a third rod 1307 with cylindrical connector 1305. Here a hexagonal connector 1306 abuts the cylindrical connector 1305 providing the modular intramedullary fixation device 1300 more stability at the fracture site of the bone (dark line in the middle portion of the bone). The distal second accordion linkage 1310 is secured to this third rod 1307 via a positioning hexagonal nut located just above the proximal end of the distal second accordion linkage 1310. The proximal first accordion linkage 1303 is secured to the first rod 1304 by a hexagonal nut located at its proximal end. Both the proximal first accordion linkage 1303 and the distal second accordion linkage 1310 are shown expanded such they are secured in place within structure of the bone. The distal end of the third rod 1307 is connected to a fourth distal rod 1309 using a hexagonal connector 912. All hexagonal connectors 1302, 1306, and 1308 and cylindrical connector 1305 are threaded at both their respective ends to receive their respective portions of the rods as shown in FIG. 26. A slight modification from previous embodiments with the two accordion linkages is that in the embodiment of FIG. 26, the positions on the rods 1307, 1304 where the accordion linkages 1310, and 1303 are respectively secured further include threading on the external surfaces for adjusting the position of the linkages thereon.

Figure 27:
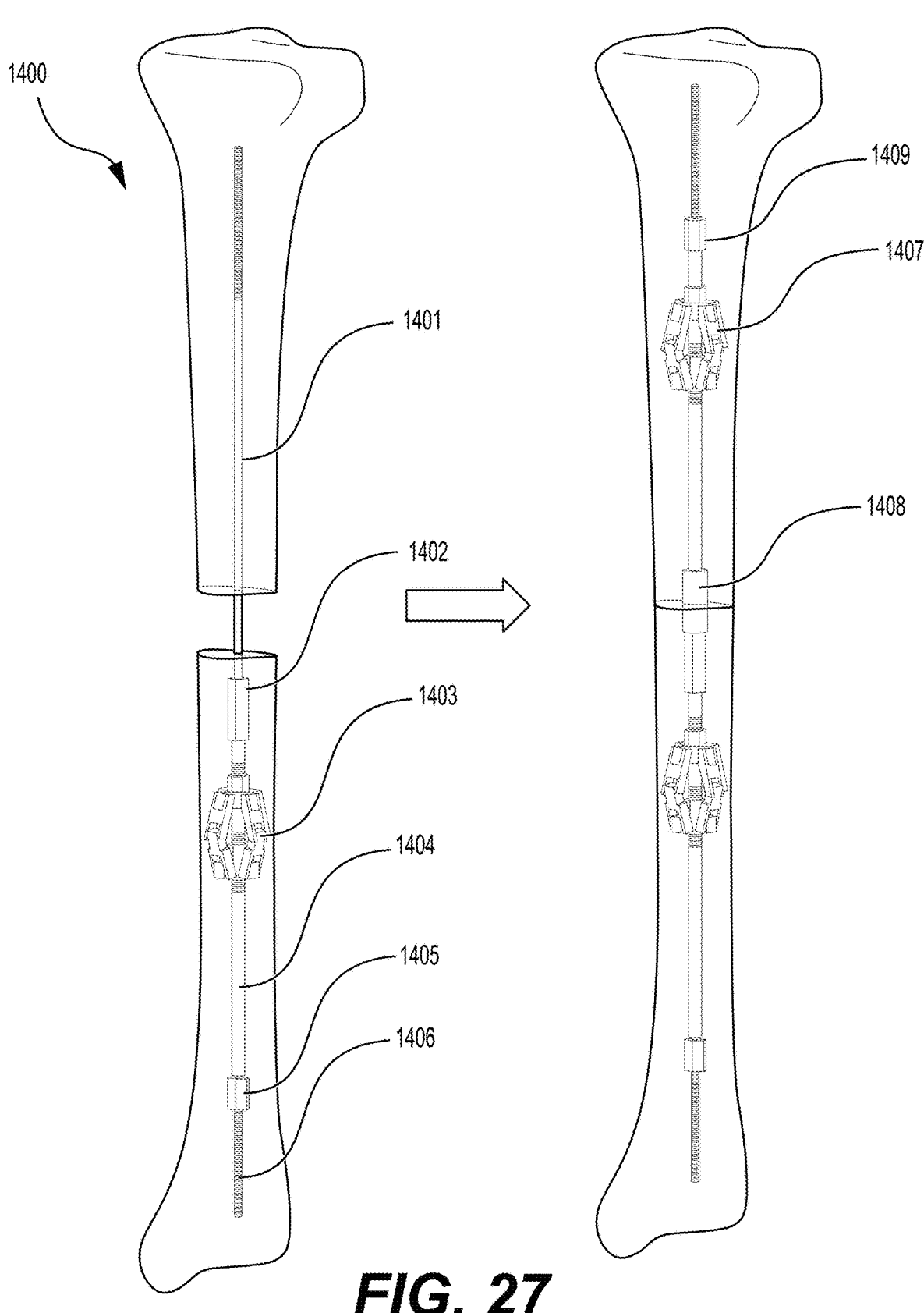
FIG. 27 is a detailed view of two alternative configurations of the second (centermost) embodiment of the modular intramedullary fixation device of FIG. 21 as inserted within the bone and as shown completely healing the break within the bone.

FIG. 27 discloses a process of modifying a first embodiment (leftmost) of FIG. 21 with the addition of parts such that it can be easily configured to be implemented as a second embodiment of FIG. 21. In FIG. 27, the modular intramedullary fixation device 1400 discloses the use of one distal accordion linkage 1403 in an expanded configuration that is secured near a proximal end of an intermediary rod 1404. The proximal end of the intermediary rod 1404 is connected to distal end of a proximal rod 1401 at a distal first hexagonal connector 1402, and the distal end of intermediary rod 1404 is connected to proximal end of a distal third rod 1406 with hexagonal connector 1405. The proximal end of proximal rod Both the hexagonal connectors 1402 and 1405 are threaded at both their respective ends to receive their respective portions of the rods as shown in FIG. 27. With addition of additional elements the first (leftmost) embodiment of FIG. 27 can be easily modified to the second (centermost) embodiment of the modular intramedullary fixation device 800 as shown in FIG. 21. In FIG. 27, the second (rightmost) embodiment includes a modular intramedullary fixation device 1400 which has additional elements mounted in place of the proximal rod 1401 of the first (leftmost) embodiment of the modular intramedullary fixation device 1400. The additional elements include a proximal first accordion linkage 1407 in addition to the distal second accordion linkage where accordion linkage 1407 is positioned proximally above the bone fracture site (dark line in the middle portion of the bone) while the distal second accordion linkage is positioned distally below the bone fracture site (dark line in the middle portion of the bone). This additional rod and linkage configuration further includes a proximal end of a first rod that is connected to a distal end of a second rod at a proximal hexagonal connector 1409, and the distal end of first rod is connected to proximal end of a third rod with cylindrical connector and hexagonal connector abutting the cylindrical connector 1408. The distal second accordion linkage is secured to this third rod via a positioning hexagonal nut located just above the proximal end of the distal second accordion linkage. The proximal first accordion linkage 1407 is secured to the first rod by a hexagonal nut located just above the proximal end of the proximal first accordion linkage. Both the proximal first accordion linkage 1407 and the distal second accordion linkage are shown expanded as they are secured in place within structure of the bone. The distal end of the third rod is connected to a fourth distal rod using a hexagonal connector. All three hexagonal connectors 1402, 1406, and 1409, and cylindrical connector 1408 are threaded at both their respective ends to receive their respective portions of the rods as shown in FIG. 21. A slight modification from previous embodiments with the two accordion linkages is that in the embodiment of FIG. 27, the positions on the rods 1307, 1304 where the accordion linkages 1310, and 1303 are respectively secured further include threading on the external surfaces for adjusting the position of the linkages thereon.

Figure 28:
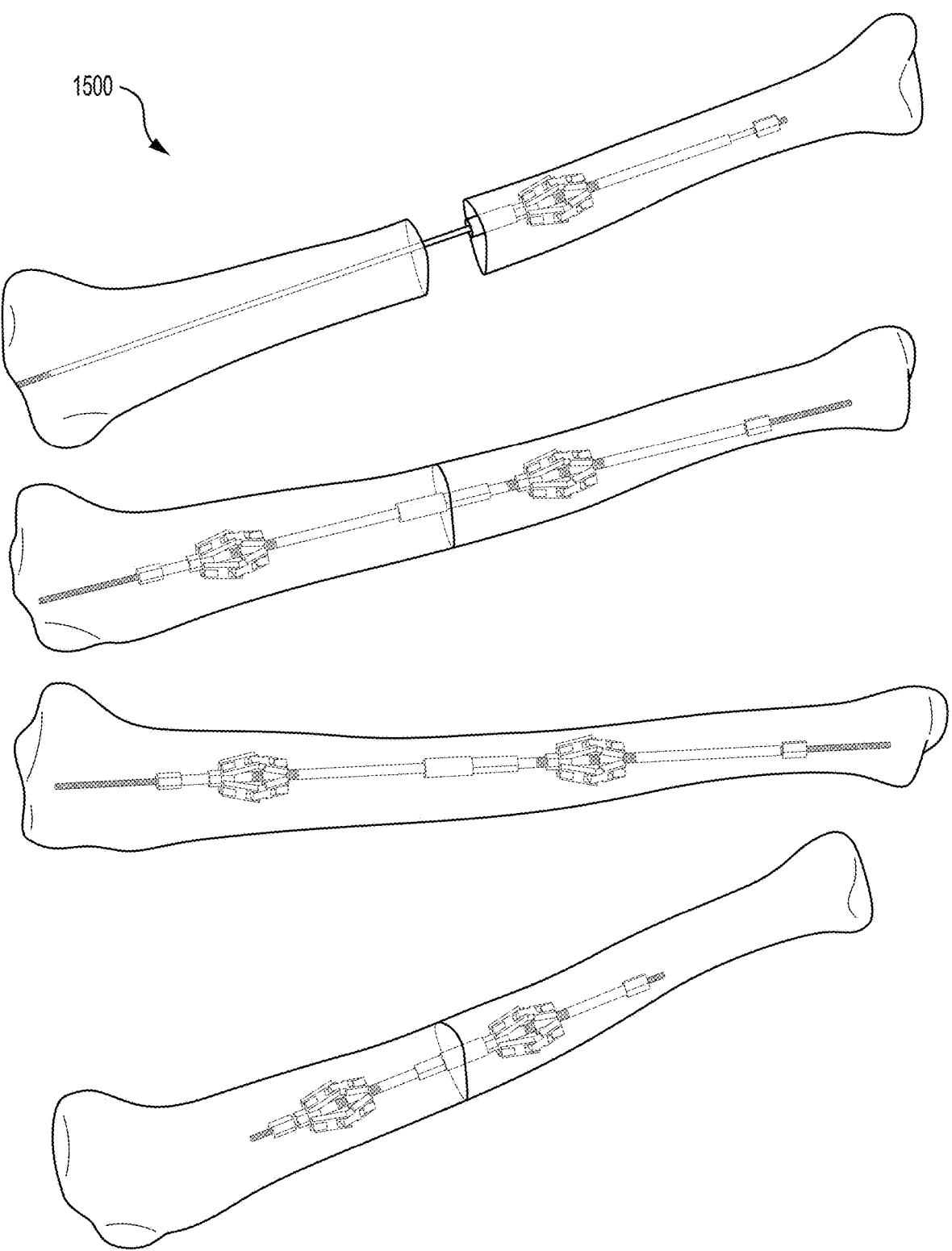
FIG. 28 is a detailed view of the second (centermost) embodiment of the modular intramedullary fixation device of FIG. 21 shown in a progression inserted within the fractured bone with just one connector to being inserted within the bone with two connectors completely healing the break within the bone.

FIG. 28 shows a progression in the use of the modular intramedullary fixation device 1400 as shown in FIG. 27 in stages of treatment. In FIG. 28, the modular intramedullary fixation device 1200 is made up of two major portions, a first proximal rod and accordion linkage combination joined with a second rod and linkage combination. FIG. 28 shows a series of images showing the progression of the treating of a bone fracture using the modular intramedullary fixation device 1500. In FIG. 28 proceeding from top to bottom is the depiction of the various stages of bone fracture healing. The first stage shows the insertion of the second distal rod and accordion linkage combination into the bone fragment below the break (dark line in the middle portion of the bone). The second stage shows the insertion of the proximal first rod and accordion linkage combination into the bone fragment above the break and further depicts the connection of the proximal first rod and accordion linkage combination in the bone fragment above the break with the second distal rod and accordion linkage combination into the bone fragment below the break such that the bone fragments are brought into proper alignment for healing. The third stage shows the continued healing and stabilization of the bone fragments. The four stage depicts the connection of the proximal first rod and accordion linkage combination in the bone fragment above the break with the second distal rod and accordion linkage combination into the bone fragment below the break such that the bone fragments are brought into proper alignment for healing and also shows the completion of the healing process where the first bone fragment and the second bone fragment have joined together and healed the break. In this final fourth stage, the length of connection of the proximal first rod and accordion linkage combination in the bone fragment above the break with the second distal rod and accordion linkage combination into the bone fragment below the break is shortened.

Figure 29:
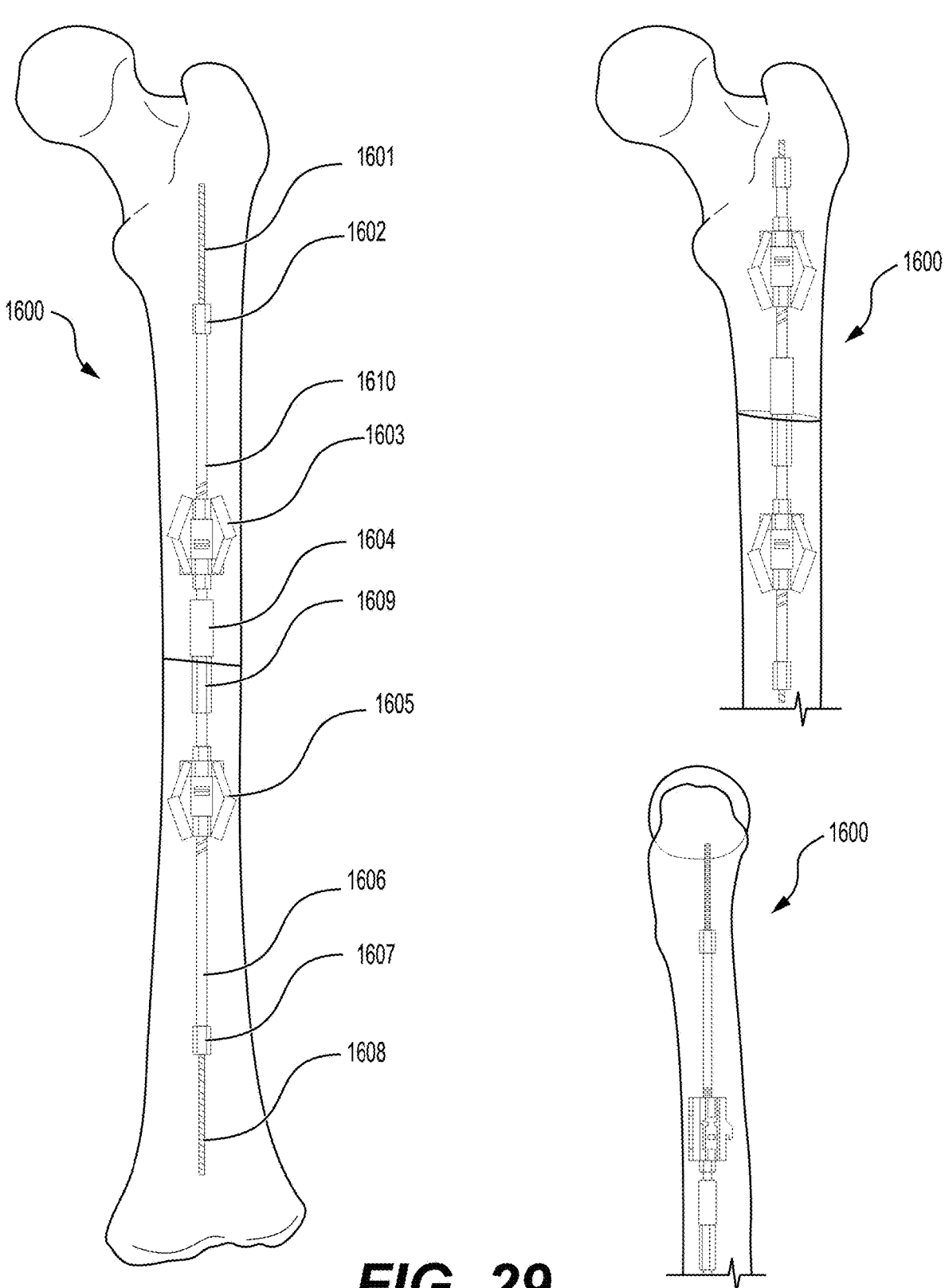
FIG. 29 is a detailed view of an alternative configuration of the second (centermost) embodiment of the modular intramedullary fixation device of FIG. 21 as inserted within the bone and as shown completely healing the break within the bone along with a top down view of the two connectors within the bone and a view of an alternative configuration of the first (leftmost) embodiment of the modular intramedullary fixation device of FIG. 21 using the connector of FIG. 23.

FIG. 29 is an alternative configuration of the second (centermost) embodiment of the modular intramedullary fixation device 800 as shown in FIG. 21 as inserted into a bone break in a femur at a midpoint of the femur. Also shown is a diagram an alternative configuration of the second (centermost) embodiment of the modular intramedullary fixation device 1600 as shown in FIG. 29, as inserted into a bone break near the head of the femur, and lastly, a side view of the femur with a top half of the modular intramedullary fixation device 1600 inserted therein is depicted. The leftmost diagram shows the modular intramedullary fixation device 1600 and also includes the use of a proximal first accordion linkage 1603 and a distal second accordion linkage 1605 where the proximal first accordion linkage 1603 is positioned above the bone fracture site (dark line in the middle portion of the bone) while distal second accordion linkage 1605 is positioned below the bone fracture site (dark line in the middle portion of the bone). This rod and linkage configuration further includes a proximal end of a first rod 1601 that is connected to a distal end of a second rod 1601 at a proximal hexagonal connector 1602, and the distal end of first rod 1610 is connected to proximal end of a third rod 1606 with cylindrical connector 1604. Here a hexagonal connector 1609 abuts the cylindrical connector 1604 providing the modular intramedullary fixation device 1600 more stability at the fracture site of the bone (dark line in the middle portion of the bone). The distal second accordion linkage 1605 is secured to this third rod 1606 via a positioning hexagonal nut located just above the proximal end of the distal second accordion linkage 1605. The proximal first accordion linkage 1603 is secured to the first rod 1610 by a hexagonal nut located at its distal end. Both the proximal first accordion linkage 1603 and the distal second accordion linkage 1605 are shown expanded such they are secured in place within structure of the bone. The distal end of the third rod 1606 is connected to a fourth distal rod 1608 using a hexagonal connector 1607. All hexagonal connectors 1602, 1607, 1609, and cylindrical connector 1604 are threaded at both their respective ends to receive their respective portions of the rods as shown in FIG. 26. A slight modification from previous embodiments with the two accordion linkages is that in the embodiment of FIG. 29, the positions on the rods 1610, 1606 where the accordion linkages 1603, and 1605 are respectively secured further include threading on the external surfaces for adjusting the position of the linkages thereon.

Figure 30:
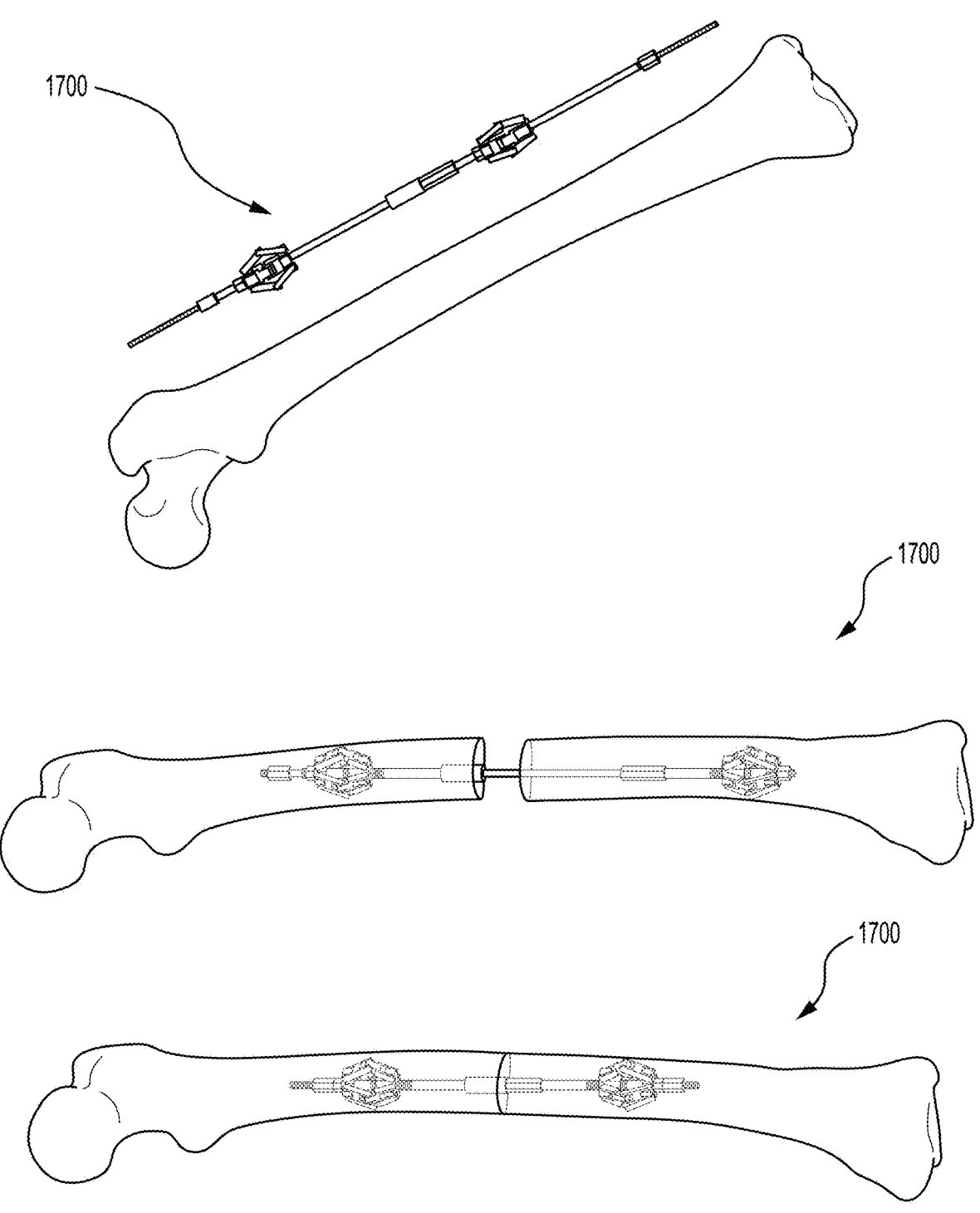
FIG. 30 is a detailed view of the second (centermost) embodiment of the modular intramedullary fixation device of FIG. 21 shown in a progression of being side by side with the bone to being inserted within the bone and completely healing the break within the bone.

FIG. 30 shows a progression in the use of the embodiment of the modular intramedullary fixation device 1600 as shown in FIG. 29. FIG. 30 shows a series of images showing the progression of the treating of a bone fracture using the modular intramedullary fixation device 1700. In FIG. 30 proceeding from top to bottom is the depiction of the various stages of bone fracture healing. The first stage is ensuring that prior to insertion the combined length of the modular intramedullary fixation device 1700 can be accommodated by the lengths of the fractured bone segments. The second stage shows the insertion of the modular intramedullary fixation device 1700 with one accordion linkage above the femur's midpoint bone break and other accordion linkage below the femur's midpoint bone break (dark line in the middle portion of the bone). The third stage shows the completion of the healing process where the first bone fragment and the second bone fragment have joined together and have completely healed the break. In this final third stage, the length of connection of the proximal first rod and accordion linkage combination in the bone fragment above the break with the second distal rod and accordion linkage combination into the bone fragment below the break is shortened.

Figure 31:
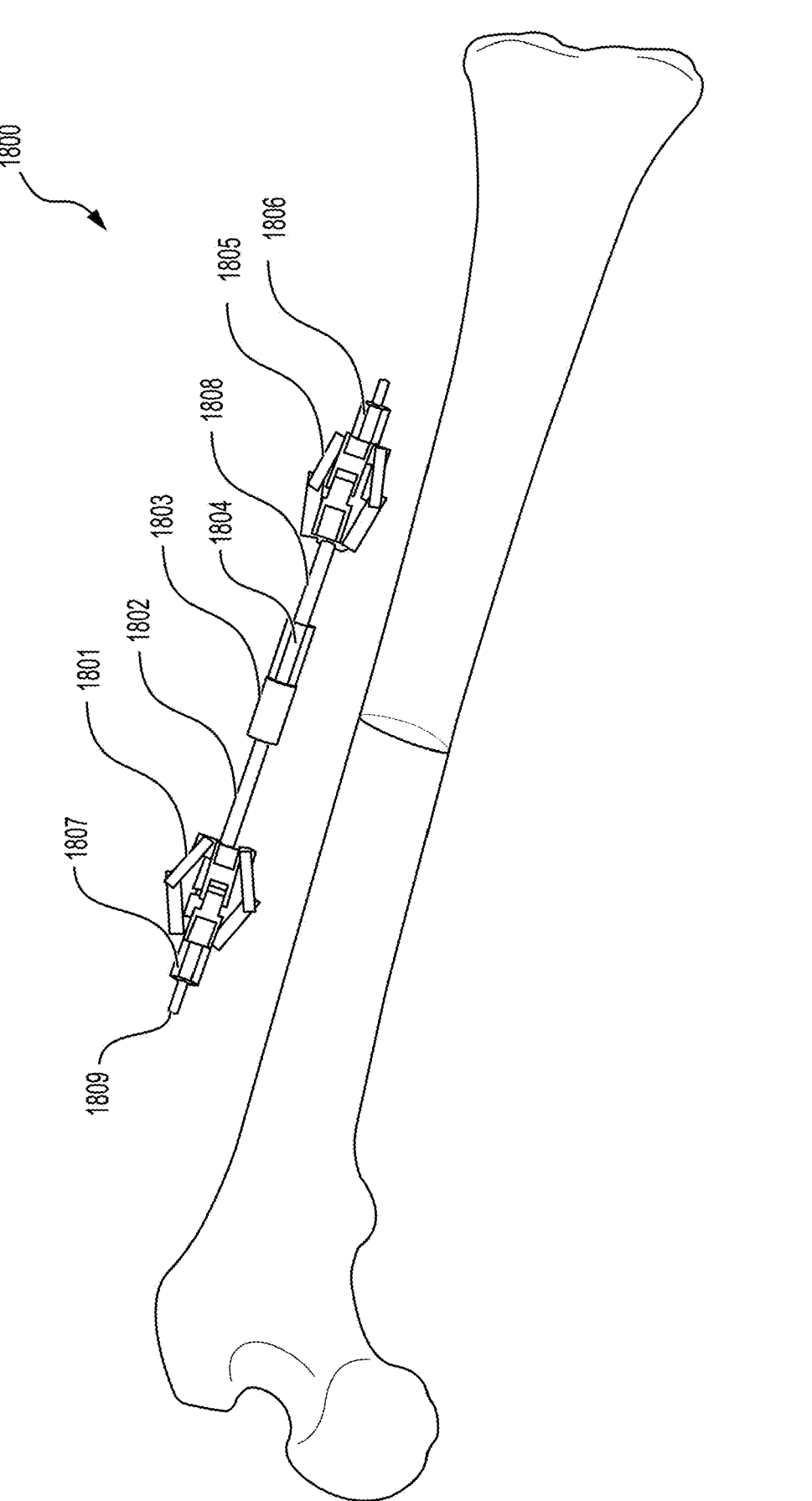
FIG. 31 is a detailed view of the second (centermost) embodiment of the modular intramedullary fixation device of FIG. 21 shown in a progression of being side by side with the bone after completely healing the break within the bone.

FIG. 31 depicts an additional modification to showing a progression in the use of the embodiment of the modular intramedullary fixation device 1600 as shown in FIG. 29. In particular, FIG. 31 is a modification of the first stage of FIG. 30 which further ensures that when configured to be at its shortest length prior to its insertion the combined length of the modular intramedullary fixation device 1800 can be accommodated by the lengths of the fractured bone segments. FIG. 31 is an alternative configuration of the second (centermost) embodiment of the modular intramedullary fixation device 800 as shown in FIG. 21. The modular intramedullary fixation device 1800 also includes the use of a proximal first accordion linkage 1801 and a distal second accordion linkage 1805 where the proximal first accordion linkage 1801 would be positioned above the bone fracture site (dark line in the middle portion of the bone) while distal second accordion linkage 1805 would be positioned below the bone fracture site (dark line in the middle portion of the bone). This rod and linkage configuration further includes a proximal end of a first rod 1802 that is connected to a distal end of a second rod 1809 at a proximal hexagonal connector 1807, and the distal end of first rod 1802 is connected to proximal end of a third rod 1808 with cylindrical connector 1803. Here a hexagonal connector 1804 abuts the cylindrical connector 1803 providing the modular intramedullary fixation device 1800 more stability at the fracture site of the bone (dark line in the middle portion of the bone). The distal second accordion linkage 1805 is secured to this third rod 1808 via a positioning hexagonal nut 1806 located at the distal end of the distal second accordion linkage 1805. The proximal first accordion linkage 1603 is secured to the first rod 1807 by a hexagonal nut located at the proximal first accordion linkage's 1801 proximal end. Both the proximal first accordion linkage 1801 and the distal second accordion linkage 1805 are shown expanded such as they would be when secured in place within structure of the femur. The distal end of the third rod 1808 is connected to a fourth distal rod using the hexagonal connector 1806. All hexagonal connectors 1804, 1806, 1807 and cylindrical connector 1803 are threaded at both their respective ends to receive their respective portions of the rods as shown in FIG. 31.

Figure 32:
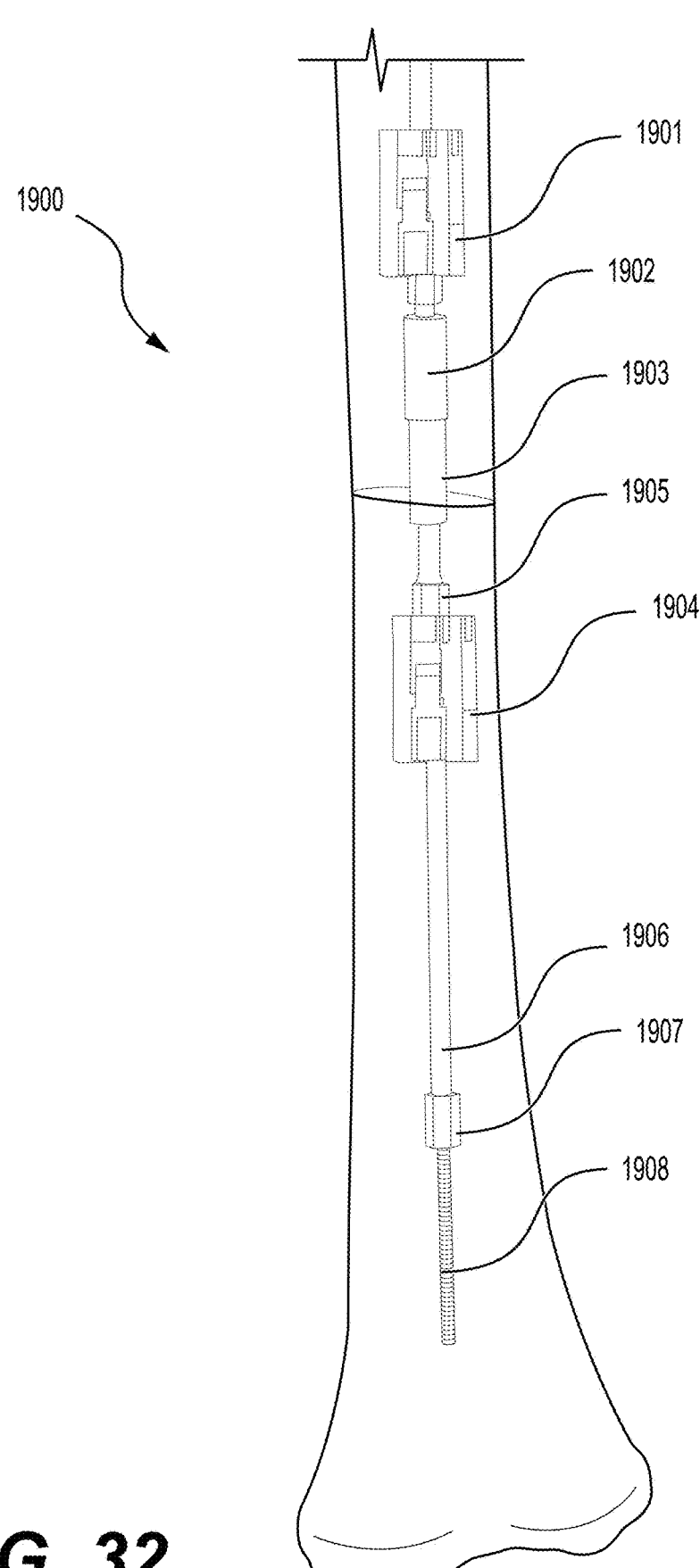
FIG. 32 is a detailed view of the first (leftmost) embodiment of the modular intramedullary fixation device of FIG. 21 shown being completed inserted within a bone fracture using a two connector configuration of the connectors in FIG. 23.
Figure 33:
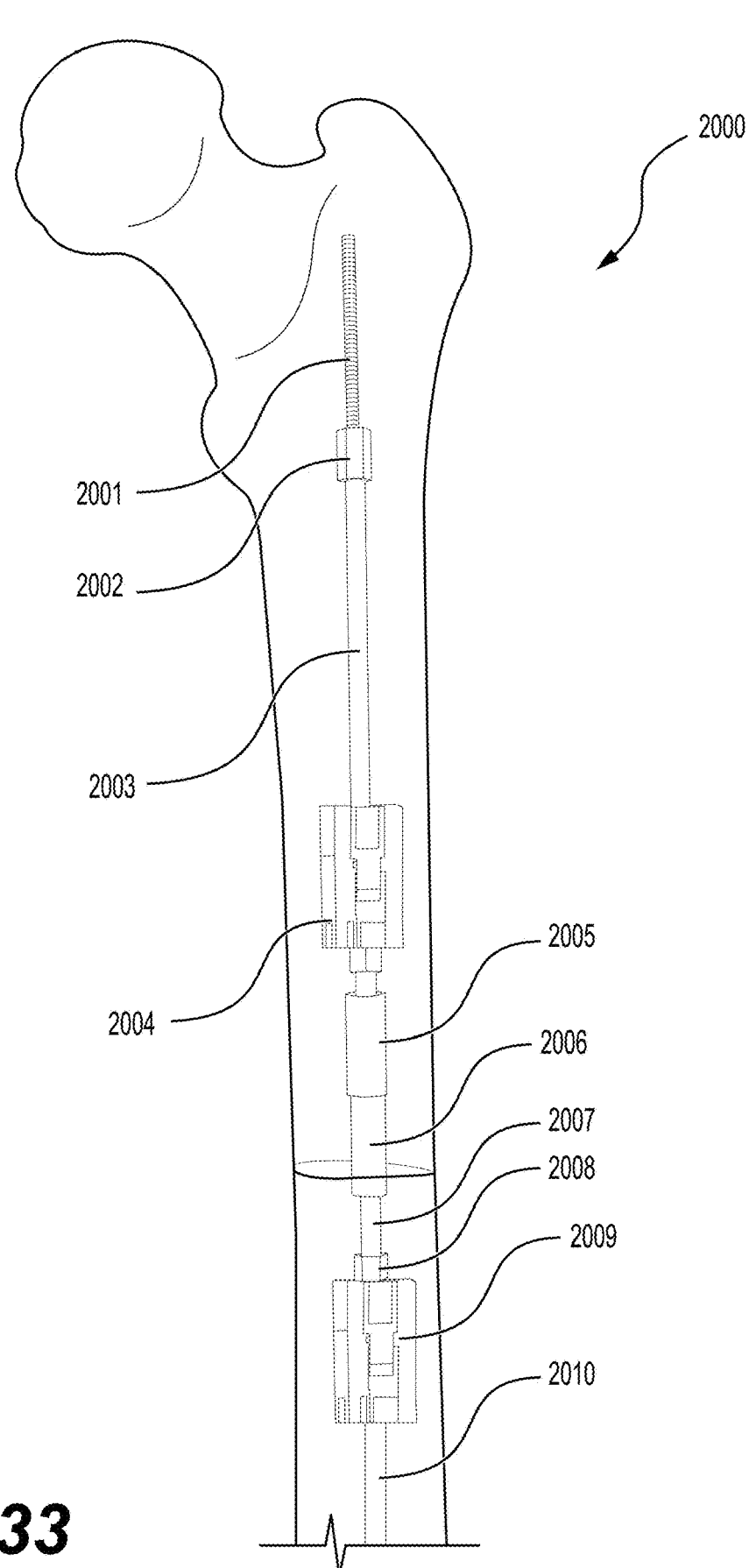
FIG. 33 is a detailed view of a modification to the first (leftmost) embodiment of the modular intramedullary fixation device of FIG. 21 shown being completed inserted within a bone fracture using a two connector configuration of the connectors in FIG. 23.

FIGS. 32 and 33 depict an additional modification to the embodiment of the modular intramedullary fixation device 1600 as shown in FIG. 29 as inserted into the a bone break in a femur at a midpoint of the femur. FIGS. 32 & 33 when combined provide an expanded view of the modular intramedullary fixation device. In FIG. 32, the modular intramedullary fixation device 1900 is shown in detail being inserted into the femur below the bone break (dark line in the middle portion of the bone). Companion FIG. 33 shows the same intramedullary fixation device 2000 as the modular intramedullary fixation device 1900 in FIG. 32, but this one depicts the insertion of the modular intramedullary fixation device 2000 above the bone break of the femur (dark line in middle portion of the bone). FIG. 32 discloses the modular intramedullary fixation device 1900 and also includes the use of a proximal first accordion linkage 1901 and a distal second accordion linkage 1904 where the proximal first accordion linkage 1901 is positioned above the bone fracture site (dark line in the middle portion of the bone) while distal second accordion linkage 1904 is positioned below the bone fracture site (dark line in the middle portion of the bone). As shown in FIG. 33, this rod and linkage configuration further includes a proximal end of a first rod 2003 that is connected to a distal end of a second rod 2001 at a proximal hexagonal connector 2002, and the distal end of first rod 2003 is connected to proximal end of a third rod (FIG. 32, element 1906 or FIG. 33, element 2010) in with cylindrical connectors (FIG. 32, elements 1902, 1903 or FIG. 33, elements 2005, 2006). The distal second accordion linkage (FIG. 32, element 1904 or FIG. 33, element 2009) is secured to this third rod (FIG. 32, element 1906 or FIG. 33, element 2010) via a positioning hexagonal nut (FIG. 32, element 1905 or FIG. 33, element 2008) located just above the proximal end of the distal second accordion linkage (FIG. 32, element 1904 or FIG. 33, element 2009). The proximal first accordion linkage (FIG. 32, element 1901 or FIG. 33, element 2004) is secured to the first rod 2003 by a hexagonal nut located at its distal end. Both the proximal first accordion linkage (FIG. 32, element 1901 or FIG. 33, element 2004) and the distal second accordion linkage (FIG. 32, element 1904 or FIG. 33, element 2009) are shown collapsed as they are secured in place within structure of the bone. The distal end of the third rod (FIG. 32, element 1906 or FIG. 33, element 2010) is connected to a fourth distal rod 1908 using a hexagonal connector 1907. All hexagonal connectors 1907, 2002 and cylindrical connectors (FIG. 32, elements 1902, 1903 or FIG. 33, elements 2005, 2006) are threaded at both their respective ends to receive their respective portions of the rods as shown in FIGS. 32-33.

FIGS. 34 and depicts an additional modification to the embodiment of the modular intramedullary fixation device 1600 as shown in FIG. 29 as inserted into a bone break in a femur at a midpoint of the femur, is actually an alternative configuration of the modular intramedullary fixation device 1900 as shown in FIG. 32. This alterative configuration of the modular intramedullary fixation device 2100 replaces the cylindrical connector (FIG. 32, element 1903 or FIG. 33, element 2006) with a hexagonal connector 2101. Here a hexagonal connector 2101 which abuts the cylindrical connector (FIG. 32, element 1902 or FIG. 33, element 2005) provides the modular intramedullary fixation device 2100 more stability at the fracture site of the bone (dark line in the middle portion of the bone). FIG. 34 discloses the modular intramedullary fixation device 2100 and also includes the use of a distal second accordion linkage 2104 where the distal second accordion linkage 2104 is positioned below the bone fracture site. The distal second accordion linkage 2104 is secured to a third rod 2105 via a positioning hexagonal nut 2103 located just above the proximal end of the distal second accordion linkage 2104. The distal second accordion linkage 2104 is shown collapsed as it is secured in place within structure of the bone. The distal end of the third rod 2105 is connected to a fourth distal rod 2107 using a hexagonal connector 2106. All hexagonal connectors 2101, 2106 are threaded at both their respective ends to receive their respective portions of the rods as shown in FIG. 34.

Each of the previous embodiments may be implemented using a bone graft material. In the further alternative embodiment of FIG. 21, the modular intramedullary fixation device 1400 may be formed from metal, such as, for example, a titanium-vanadium composite.

It is to be understood that the modular intramedullary fixation devices are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A modular intramedullary fixation device, comprising:
a plurality of substantially Z-shaped modular elements, wherein each of the substantially Z-shaped modular elements has a proximal flange and a distal flange, the distal flange of each of the substantially Z-shaped modular elements being secured to the proximal flange of an adjacent one of the substantially Z-shaped modular elements;
a proximal end piece secured to the proximal flange of a proximal-most one of the substantially Z-shaped modular elements; and
a distal end piece secured to the distal flange of a distal-most one of the substantially Z-shaped modular elements, and
wherein the proximal end piece and a first portion of the substantially Z-shaped modular elements define a proximal section of the modular intramedullary fixation device, and the distal end piece and a second portion of the substantially Z-shaped modular elements define a distal section of the modular intramedullary fixation device, a maximum width of the proximal section being greater than a maximum width of the distal section,
wherein the proximal section of the modular intermedullary fixation device further comprises a plurality of substantially Z-shaped modular elements that define a first concave curved surface on the proximal section of the modular intermedullary fixation and a plurality of substantially Z-shaped modular elements that define a first flat surface on the proximal section on the intermedullary device, said first concave curved surface adjacent said first flat surface,
wherein the first concave curved surface has a starting edge defined by the proximal end piece secured to the proximal flange of the proximal-most one of the substantially Z-shaped modular elements and an ending edge defined by the maximum width of the proximal section,
wherein the distal section of the modular intermedullary fixation device further comprises a plurality of substantially Z-shaped modular elements that define a second concave curved surface on the distal section of the modular intermedullary fixation and a plurality of substantially Z-shaped modular elements that define a second flat surface on the distal section on the intermedullary device, said second concave curved surface adjacent said second flat surface, and
wherein the second concave curved surface has a starting edge defined by the distal end piece secured to the distal flange of the distal-most one of the substantially Z-shaped modular elements and an ending edge defined by the maximum width of the distal section.

2. The modular intramedullary fixation device as recited in claim 1, further comprising a plurality of screws, wherein each of the proximal and distal end pieces has a passage formed therethrough for receiving a corresponding one of the plurality of screws, wherein the proximal flange of each 5 of the substantially Z-shaped modular elements has a passage formed therethrough for receiving a corresponding one of the plurality of screws, and wherein the distal flange of each of the substantially Z-shaped modular elements has a passage formed therethrough for receiving a corresponding 10 one of the plurality of screws for securing the plurality of substantially Z-shaped modular elements, the proximal end piece and the distal end piece together.

\*  \*  \*  \*  \*

15